(12) United States Patent
Martel-Pelletier et al.

(10) Patent No.: US 7,555,153 B2
(45) Date of Patent: Jun. 30, 2009

(54) NON-INVASIVE JOINT EVALUATION

(75) Inventors: Johanne Martel-Pelletier, Saint-Lambert (CA); Jean Pierre Pelletier, Saint-Lambert (CA); Fabrice Ganansia, Palaiseau (FR); Françoys Labonté, Longueuil (CA); François Abram, Montreal (CA); Jean-Pierre Raynauld, Boucherville (CA)

(73) Assignee: Arthrovision Inc., Montreal (CA)

( * ) Notice: Subject to any disclaimer, the term of this patent is extended or adjusted under 35 U.S.C. 154(b) by 810 days.

(21) Appl. No.: 11/003,970

(22) Filed: Dec. 3, 2004

(65) Prior Publication Data

US 2006/0002600 A1   Jan. 5, 2006

Related U.S. Application Data

(60) Provisional application No. 60/584,663, filed on Jul. 1, 2004.

(51) Int. Cl.
  *G06K 9/00* (2006.01)
  *A61K 35/34* (2006.01)
  *A61F 2/30* (2006.01)

(52) U.S. Cl. ........................ 382/131; 382/128; 424/548; 623/18.11

(58) Field of Classification Search ................ 382/128, 382/129, 130, 131, 132, 133, 134; 600/216, 600/410, 411, 415, 421, 546, 562; 378/208; 607/48; 623/14.13, 18.11, 19.11, 19.12, 623/20.11, 20.12, 20.13, 20.14, 23.5, 23.76, 623/23.39; 530/841; 424/548; 128/920, 128/922
See application file for complete search history.

(56) References Cited

U.S. PATENT DOCUMENTS

| | | | |
|---|---|---|---|
| 5,509,042 A * | 4/1996 | Mazess | 378/54 |
| 5,647,361 A * | 7/1997 | Damadian | 600/411 |
| 5,743,264 A | 4/1998 | Bonutti | |
| 6,044,289 A * | 3/2000 | Bonutti | 600/415 |
| 6,560,476 B1 | 5/2003 | Pelletier et al. | |
| 6,596,225 B1 * | 7/2003 | Pope et al. | 419/11 |

(Continued)

OTHER PUBLICATIONS

Cohen, Z.A., Moa-Anderson, B.J., Hepinstall, M.S., Levine, W.N., Mow, V.C., and Ateshian, G.A., "Templates of Normal Patellofemoral Joint Cartilage Thickness and Tools for the Detection of Cartilage Lesions in Patients with Osteoarthritis," Poster Session - Cartilage - Hall E - 47$^{th}$ Annual Meeting, Orthopaedic Research Society, Feb. 25-28, 2001, San Francisco, California.

(Continued)

*Primary Examiner*—Abolfazl Tabatabai
(74) *Attorney, Agent, or Firm*—Kristofer E. Elbing

(57) ABSTRACT

Disclosed, in one general aspect, is a musculoskeletal imaging system that includes a source of feature data extracted from imaging data resulting from imaging acquisitions from joints of different individuals affected by different diseases, and this feature data includes disease characteristic categorization information for a plurality of disease categories. A comparison module is operative to compare patient imaging data resulting from an imaging acquisition from a joint of a patient with the feature data. The comparison module is also operative to provide at least one categorization indicator for the patient imaging data that indicates a correspondence between spatial information in the patient imaging data and the disease categories for which there is extracted categorization information in the feature data.

49 Claims, 15 Drawing Sheets

U.S. PATENT DOCUMENTS 6,901,280 B2    5/2005    Pelletier et al.

OTHER PUBLICATIONS

Cohen, Z.A., Mow, V.C., Henry, J.H., Levine, W.N., and Ateshian, G.A., "Templates of the Cartilage Layer of the Patellofemoral Joint and Their Use in the Assessment of Osteoarthritic Cartilage Damage," *Osteoarthritis and Cartilage*, 11 (2003), pp. 569-579.

Davies, Rhodri H., Twinning, Carole J., Cootes, Tim F., Waterton, John C., and Taylor, Chris J., "3D Statistical Shape Models Using Direct Optimisation of Description Length," in A. Heyden et al. (Eds.) ECCV 2002, LNCS 2352, Berlin:Springer-Verlag (2002), pp. 3-20.

Davies, Rh.H., Cootes, T.F., Twinning, C.J., Waterton, J.C., and Taylor, C.J., "3D Statistical Shape Models for Automatic Segmentation of MR Images," in Proceedings of the *International Society for Magnetic Resonance in Medicine (ISMRM )* 10 (2002).

Snedecor, George W. and Cochran, William G., *Statistical Methods* $8^{th}$ edition, Iowa State University Press, 1989, pp. 36-37.

Warfield, Simon K., Jolesz, Ferenc A., and Kikinis, Ron, "A High Performance Computing Approach to the Registration of Medical Imaging Data," *Parallel Computing* 24 (1998), pp. 1345-1368.

U.S. Appl. No. 11/003,620, filed Dec. 3, 2004, Cont. of Pelletier patents.

U.S. Appl. No. 11/003,942, filed Dec. 3, 2004, Cont. of Pelletier patents.

Cootes, T.F., Taylor, C. J., Cooper, D.H., and Graham, J. "Active Shape Models - Their Training And Application," *Computer Vision and Image Understanding*, 61(1): 389, Jan. 1995.

Cootes, T.F. and Taylor, C.J., "Statistical Models Of Appearance For Medical Image Analysis And Computer Vision," in *Proc. SPIE Medical Imaging*, 2001.

MacQueen, J.B., "Some Methods For Classification And Analysis Of Multivariate Observations," in: *Proceedings of $5^{th}$ Berkeley Symposium on Mathematical Statistics and Probability, 1*, University of California Press, Berkeley, CA, (1967), pp. 281-297.

Solloway, S. Taylor, C. J., Hutchinson, C. E., and Waterton, J. C. "Quantification Of Articular Cartiage From MR Images Using Active Shape Models," in $4^{th}$ *European Conference on Computer Vision*, Cambridge, England, (1996), pp. 400-412.

Stammberger et al., "Determination of 3d Cartilage Thickness Data from MR Imaging: Computational Method and Reproducibility in the Living", *Magnetic Resonance in Medicine*, Wiley, USA, Mar. 1999, pp. 529-536.

Williams, Tomos G., Taylor, Christopher J., Gao, ZaiXiang, and Waterton, John C. "Corresponding Articular Cartilage Thickness Measurements In The Knee Joint By Modelling The Underlying Bone," in Chris Taylor and J. Alison Noble (Eds.), *IPMI 2003 Proc. 18th Int. Conf. on Information Processing in Medical Imaging, Lecture Notes in Computer Science 2732*, Springer: Ambleside, UK, Jul. 2003, pp. 126-135.

Wolf et al: "Automatic segmentation and 3D-registration of a femoral bone in MR images of the Knee", *4th Open German-Russian Workshop on Pattern Recognition*, Valday, Russia, Mar. 3, 1996. "Pattern Recognition and Image Analysis", whole document.

\* cited by examiner

NON-INVASIVE JOINT EVALUATION

CROSS-REFERENCE TO RELATED APPLICATION

This application claims the benefit of U.S. Provisional Application No. 60/584,663, filed Jul. 1, 2004, which is herein incorporated by reference.

FIELD OF THE INVENTION

This invention relates to methods and apparatus for evaluating the condition of one or more joints of a patient using a non-invasive data acquisition technique, such as Magnetic Resonance Imaging (MRI).

BACKGROUND OF THE INVENTION

Osteoarthritis (OA) is a prevalent disease characterized mainly by cartilage degradation that is clinically reflected by a gradual development of joint pain, stiffness, and loss of motion. Osteoarthritis is extremely frequent in the general population, and it is estimated that its radiological prevalence is close to 50% overall. This figure is even higher in the elderly, with as much as 75% of the population between ages of 55 and 64 exhibiting some degree of radiological osteoarthritis in one or more joints. Although this disease is often benign, severe degenerative changes may cause serious disability.

The early stages of osteoarthritis are relatively asymptomatic. Patients then begin to experience mild symptoms, such as morning stiffness, pain with activity, and mild swelling. In later stages, the frequency and intensity of pain tends to increase, and there can be a progressive loss of joint function.

Current non-surgical treatment regimens focus on maintaining function and decreasing symptoms. These can include the use of anti-inflammatory medications, exercise programs, weight control, and occasionally steroid injections. Beginning these regimens at earlier stages may delay the onset of more serious symptoms, and can in some cases even postpone or eliminate the need for surgery.

Promising research is also under way to find a therapeutic agent that will slow or stop the progression of the disease. But it is unlikely that this research will yield an agent that will actually reverse the progression of the disease. Even if current efforts are successful in identifying suitable therapeutic agents, therefore, the overall comfort levels and joint function levels achievable with these agents will most likely still depend on early and accurate diagnosis.

SUMMARY OF THE INVENTION

In one general aspect, the invention features a musculoskeletal imaging system that includes a source of feature data extracted from imaging data resulting from imaging acquisitions from joints of different individuals affected by different diseases, and this feature data includes disease characteristic categorization information for a plurality of disease categories. A comparison module is operative to compare patient imaging data resulting from an imaging acquisition from a joint of a patient with the feature data. The comparison module is also operative to provide at least one categorization indicator for the patient imaging data that indicates a correspondence between spatial information in the patient imaging data and the disease categories for which there is extracted categorization information in the feature data.

In preferred embodiments, The source of feature data can be operative to provide feature data for at least some individuals having healthy cartilage. The source of feature data can be operative to provide feature data that expresses information for a plurality of patients that has been normalized and aggregated. The source of feature data can be operative to provide feature data that expresses information for a plurality of patients that has been normalized, aggregated, and compressed. The source of feature data can be operative to provide feature data that expresses information for a plurality of patients that has been normalized and averaged. The source of feature data can be operative to provide feature data that expresses information for a plurality of segmented patient scans that have been normalized and aggregated. The source of feature data can be operative to provide feature data that expresses information for a plurality of segmented patient scans that have been normalized, aggregated, and compressed. The comparison module can be further operative to provide a confidence level for the categorization indicator. The system can further include a follow-up module operative to identify trends in changes to the categorization indicator over time. The system can further include an outgoing communication interface responsive to the comparison module and operative to provide the categorization indicator to a remote location. The source of patient imaging data can comprise part of an incoming communication interface. The system can further include an aggregate result analysis module operative to perform statistical analysis of results from the comparison module for a plurality of patients. The aggregate result analysis module can include correlative logic operative to determine relationships between treatment methods and categorization indicators for the plurality of patients. The system can further include a classification adjustment module responsive to the comparison module and operative to adjust the categorization information based on results from the comparison module. The disease characteristic categorization information can include a plurality of subcategories for different patient groupings. The subcategories can be based on symptom groupings. The subcategories can be based on patient demographic groupings. The feature data can further include further patient characteristics extracted from additional sources. The further patient characteristics can include patient demographic information. The further patient characteristics can include patient symptom information. The source of feature data can be a source of imaging data resulting from statistical analysis of image data acquired from the joints affected by different diseases. The source of feature data can be a source of imaging data resulting from dispersion analysis of image data acquired from the joints affected by different diseases. The source of feature data can be a source of imaging data resulting from principal component analysis of image data acquired from the joints affected by different diseases. The source of feature data can include categorization information for a global significant cartilage loss category and for at least one localized significant cartilage loss category. The source of feature data can include categorization information for a global significant cartilage loss category, for a global cartilage loss tendency category, and for at least one localized significant cartilage loss category. The source of feature data can include categorization information for a global significant cartilage loss category, for a global cartilage loss tendency category, for a medial condyle significant loss and medial trochlea loss tendency category, and for a medial condyle significant loss, trochlea significant loss, and medial condyle loss category. The source of patient imaging data can be operative to provide a fully automatically segmented imaging data set. The source of patient imaging data can be operative to provide a imaging data set having a resolution that is significantly lower than a resolution for the acquisitions on which the feature data is based. The source of patient imaging data can include digital identifiers associated with imaging data for a particular patient. The digital identifiers can include patient identifiers, physician identifiers, and joint identifiers. The source of patient imaging data can include error correcting codes. The error correcting codes can include codes associated with imaging data for a particular patient. The source of patient imaging data can include a format identifier associated with imaging data for a particular patient. The system can further include a patient verification module. The source of patient imaging data can be a source of magnetic imaging data resulting from a magnetic resonance imaging acquisition from the joint of the patient.

In another general aspect, the invention features a musculoskeletal imaging method that includes obtaining a patient imaging data set resulting from an imaging acquisition from a joint of a patient, obtaining feature data resulting from imaging acquisitions from joints of different individuals affected by different diseases, wherein the feature data includes extracted disease characteristic categorization information for a plurality of disease categories, comparing the patient imaging data set with the feature data, and providing, based on results of the step of comparing, a categorization indicator for the patient imaging data set that indicates a correspondence between information in the patient imaging data set and the extracted disease categories for which there is extracted categorization information in the feature data.

In preferred embodiments, the method can further include the step of determining whether to indicate a treatment for the patient based on the categorization indicator. The step of determining can be operative to determine whether to indicate the use of a drug therapy. The step of determining can be operative to determine whether to indicate the use of a disease modifying osteoarthritis drug. The step of determining can be operative to determine whether to indicate the local administration of an anti-inflammatory agent. The step of determining can be operative to determine whether to indicate the use of an exercise therapy. The step of determining can be operative to determine whether to indicate surgery. The step of determining can be operative to determine whether to indicate a rehabilitation method. The method can further include the step of determining whether to admit the patient to a clinical trail based on the categorization indicator. The method can further include the step of deriving from the categorization indicator and from other categorization indicators for other patients information about a treatment performed to at least some of the patients. The method can further include the step of determining whether to indicate a sports training regimen based on the categorization indicator. The method can further include the step of comparing the categorization indicator with results from other diagnostic methods. The step of obtaining a patient imaging data set can include obtaining a magnetic resonance imaging data set resulting from a magnetic resonance imaging acquisition from the joint of the patient.

In a further general aspect, the invention features a musculoskeletal imaging system that includes means for obtaining a patient imaging data set resulting from an imaging acquisition from a joint of a patient, means for obtaining feature data resulting from imaging acquisitions from joints of different individuals affected by different diseases, wherein the feature data includes extracted disease characteristic categorization information for a plurality of disease categories, means for comparing the patient imaging data set with the feature data, and means for providing, based on results of the step of comparing, a categorization indicator for the patient imaging data set that indicates a correspondence between information in the patient imaging data set and the extracted disease categories for which there is extracted categorization information in the feature data.

Systems according to the invention are advantageous in that they can enhance the amount of information available from a patient image. Because patient image data is compared with feature data that is selectively extracted from imaging data for a number of individuals in a particular population, systems according to the invention can be made to differentiate between subtly different types of patterns of disease progression. As a result, it may be possible to obtain meaningful diagnostic information about a patient's joint from a single image, instead of waiting to measure changes over time.

Early availability of diagnostic information is important in the case of progressive joint diseases, such as OA, because it can allow for early treatment of these diseases, and thereby help to delay or avoid their later stages. Simple changes in exercise habits or weight loss, for example, may delay more severe measures, such as surgery, if they are taken at the earliest signs of disease. It may even be possible to detect changes in the joint before the patient exhibits any symptoms, and thereby delay the onset of symptoms altogether.

Diagnostic information available from systems according to the invention may also be used to more precisely target treatments prescribed for particular individuals. Some types of patterns of progression may indicate that a patient is a good candidate for a particular type of drug treatment, for example, while others may show that such treatments do not warrant the risk of side-effects or that another treatment is most likely to produce the best results. This targeting information should result in earlier, more appropriate treatment for each of the different types of progression, and should help to reduce costs associated with treatments that are inappropriately targeted.

Systems according to the invention can also be highly objective. Because they can be made to rely exclusively on an automated comparison of image information with extracted feature information for a population, bias and human error can be kept to a minimum. This objectivity is very important in designing and monitoring scientific studies and clinical trials. As a result, it may be possible to more quickly and effectively develop additional treatments for joint diseases.

Systems according to the invention may also allow diagnosis to take place from lower resolution images. Because a comparison takes place with extracted feature information from a number of different patients, it may detect information too subtle to be seen by a radiologist. Less expensive, lower resolution MRI systems may therefore be used in some diagnostic and screening settings. Alternatively, shorter acquisition times can be used for a given imaging instrument, making the acquisition more comfortable for the patient and improving the availability and throughput of the instrument.

DETAILED DESCRIPTION OF AN ILLUSTRATIVE EMBODIMENT

Figure 1:
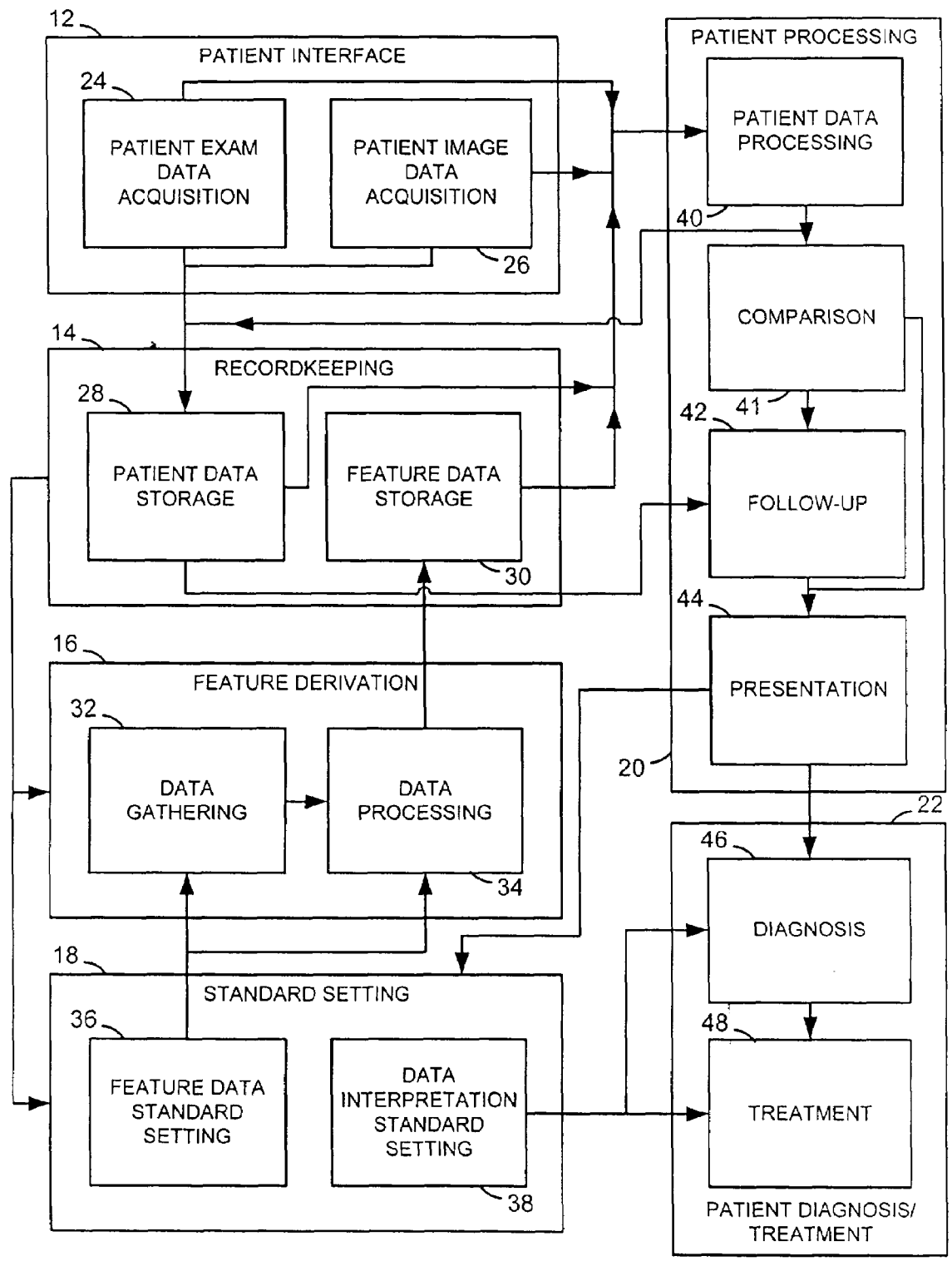
FIG. 1 is a block diagram of a joint evaluation system according to the invention.

Referring to FIG. 1, an overall joint evaluation system 10 according to the invention can include one or more of the following modules: a patient interface 12, a recordkeeping module 14, a feature derivation module 16, a standard-setting module 18, a patient data processing module 20, and a diagnosis/treatment module 22. As will be discussed in more detail below, the modules and parts thereof can be implemented by different individuals and/or organizations. One of ordinary skill in the art would also recognize that it is also possible to combine, redistribute, or even omit functions for the various modules to achieve a different breakdown.

For example, recordkeeping functions can be performed by a larger organization, such as a teaching hospital, which also performs all of the other functions of the system. In smaller office settings, the recordkeeping might be performed by an outside service provider, or an affiliated hospital. And in some implementations, such as in a mobile screening clinic, it might even be possible to perform screening functions without performing any significant storage of patient data.

The patient interface 12 can include a patient exam data acquisition interface 24 and a patient image data acquisition interface 26. The patient exam data interface is designed to receive patient data, such as would be obtained during an exam by a physician. These data can include patient demographic data, such as age, race, occupation, height, and/or weight. The patient exam data can also include symptom data, such as self-reported patient data, results of physician-administered diagnostic tests, and/or other data reflective of the patient's symptoms. These data can be entered into the system directly, or it can be relayed from other systems.

The patient image data acquisition interface 26 receives image data reflective of spatial features of the joint of the patient, such as MRI data. These data can be obtained in a variety of ways, such as by being relayed directly from an imaging system, by being transferred electronically from another hospital, from a disk, or even by digitization of hard copies. Preferably, the evaluation is performed on a patient's knee joint, but other joints could also be evaluated.

The recordkeeping interface can include patient data storage 28 and feature data storage 30. The patient data storage can store some or all of the patient exam data and/or patient image data. The feature data storage can store feature data extracted from magnetic resonance imaging data resulting from magnetic resonance imaging acquisitions from joints of different individuals in a particular population of individuals. As will be discussed in more detail below, the feature data can include disease characteristic categorization information that allows a patient's image data to be categorized.

The patient processing module 20 can include a patient data processing module 40, a comparison module 41, a follow-up module 42, and a presentation module 44. The patient data processing module 41 performs operations to convert patient image data into a format that can be compared with the feature data. Its functions can include segmentation, sub-pixel interpolation, and data projection, although other types of operations may also yield suitable results.

The comparison module 41 performs comparisons between the processed patient image data and the feature data in order to evaluate the state of the patient's joint. In the present embodiment, the functions of the patient processing module and the comparison module are kept separate, allowing results of the patient data processing module to be stored. Although this functional separation is not necessary, storing processed image data allows for further comparison operations to take place without repeating patient processing operations. It may also allow the actual patient image data, which tends to be voluminous, to be stored offline.

The follow-up module 42 can combine information from the comparison module/or the patient data processing module with prior comparison information to obtain information about how the patient's joint has changed over time. The presentation module receives information from the comparison module 41 and/or the follow-up module 42 and formats it for review by a physician, the patient, and/or other subsystems, such as the data gathering module 32 and/or the diagnosis/treatment module 48. The presentation module can create result sets that take a variety of different forms, such as an enhanced image, one or more numerical values, or a suggested diagnosis and certainty value.

The patient diagnosis/treatment module 22 can include a diagnosis module 46 and a treatment module 48. The diagnosis module can provide a diagnosis indication and a corresponding confidence level for that diagnosis indication based on the information derived by the patient data processing module 20. The treatment module can provide a treatment indication and a corresponding confidence level for that treatment indication. Both the diagnosis indication and the treatment indication should preferably be in the form of a recommendation or a cross-check for the physician. It may be possible, however, to use these indications directly in certain circumstances. Truly blind clinical trial decisions could be made in an automated fashion based on information from the diagnosis module, for example, or automated rehabilitation equipment could derive operating parameters directly from the treatment module.

The feature derivation module 16 can include a data gathering module 32 and a data processing module 34. The data gathering module can include a set of functions designed to select and/or classify population data, such as MRI data. The data processing module 34 includes logic operative to derive feature data from the population data assembled by the data gathering module.

The standard setting module 18 can include a feature data standard setting module 36 and a data interpretation standard setting module 38. The feature data standard setting module sets standards for the acquisition of data and the processing of those data into standard sets. The data interpretation standard setting module sets standards for automated diagnosis and treatment operations.

As presented above, functions of the various system modules can be performed by different organizations, which may or may not be physically close. In one embodiment, one organization publishes one or more feature data sets, making them accessible to a number of evaluation organizations, such as hospitals or other health care providers. A third organization issues standards to ensure that the feature data sets are meaningful and actions taken based on them are sufficiently safe. Other organizations can provide further services, such as imaging services, recordkeeping services, or patient data processing services.

Some of these services can be provided over communications channels, such as the internet, through well-known interfaces such as Hypertext Transfer Protocol (HTTP) or extensible Markup Language (XML). A patient data processor, for example, could receive images from a client hospital through an secure internet connection, evaluate the images based on one or more feature data sets, and then transfer a result set back to the hospital through the same channel.

Figure 2:
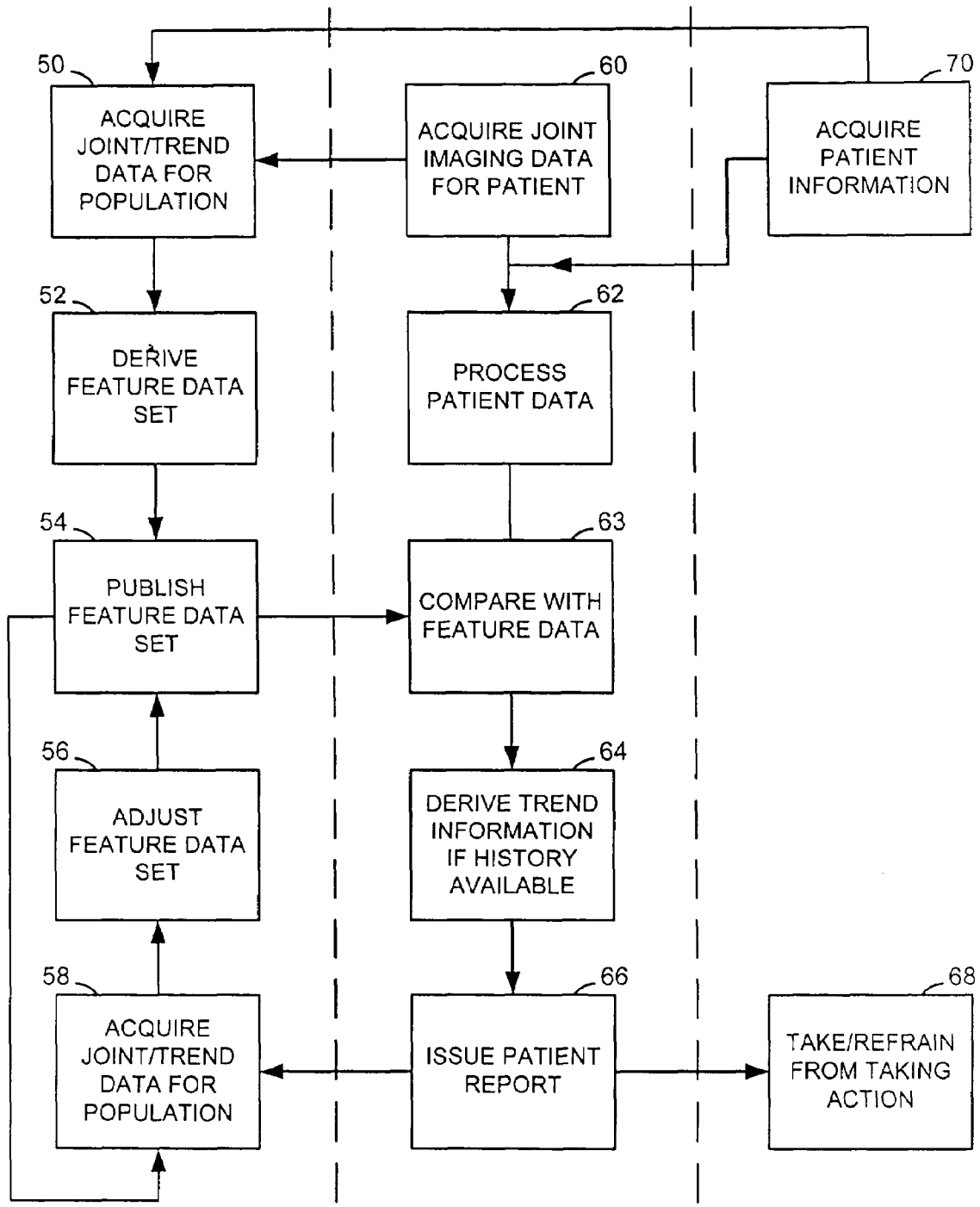
FIG. 2 is a flowchart illustrating an operation sequence for the system of FIG. 1.

Referring to FIG. 2, overall operation of the joint evaluation system 10 begins with the acquisition of joint image data for a population (step 50). This joint data includes at least one image for each member of the population, although it may also include one or more follow-up images for these individuals, as well as demographic and symptom data. Members of the population are selected based on a desired set of characteristics. It may be desirable, for example, to sample the overall population of the region or country in which the system is being used, including both healthy patients and patients exhibiting ailments in their joints. It may also be desirable to replicate the characteristics of certain age groups. And particular specialists may also find it useful to work with a population made up of patients exhibiting certain types of symptoms or diagnoses.

The system then derives one or more feature data sets from the data acquired for the population (step 52). This derivation process extracts a subset of desired information from the patient data sets. The desired information would typically be that information which is most relevant to disease categorization, although other objectives might also be satisfied with different types of extraction processes. A number of different methods could be employed to perform the feature extraction, such as principal component analysis or dispersion analysis.

Once the feature data set has been derived and evaluated, it can be made available to one or more evaluation systems (step 54). The feature data sets may also be adjusted periodically or continuously (step 56). This adjustment can include continuing to acquire and process data from new or existing members of the population of interest, and/or it can take place through the incorporation of information from evaluation of patients based on earlier models (step 58).

Joint evaluation for a particular patient begins with the acquisition of joint imaging data (step 60). This acquisition can include the acquisition of images of one or both of the patient's knee joints using an MRI imaging system. The organization evaluating the patient can perform the acquisition, or it can receive the images from another source. MRI imaging parameters suitable for joint evaluation are described, for example, in U.S. Pat. No. 6,560,476, entitled "Evaluating Disease Progression Using Magnetic Resonance Imaging," issued May 6, 2003, and herein incorporated by reference.

This methodology can be supplemented with a technique known as Active Shape Modeling (ASM). ASM is used to build a statistical shape model of the surface (or volume) to be segmented using semi-automatically segmented data as a training set. The model is composed of a mean shape and a shape variation space spawning the training set. Automatic segmentation is carried out, in the 3D image, by an alternating sequence of rigid and gradient based deformations applied to the mean shape. Before being applied to the segmented shape, deformations are projected into the model variation space so that resultant shape remains consistent with the training set. ASM is described in more detail in, for example. Active shape models—their training and application, by T. F. Cootes, C. J. Taylor, D. H. Cooper, and J. Graham, Computer Vision and Image Understanding, 61(1):389, January 1995, which is herein incorporated by reference.

The system then processes the patient data, including the joint imaging data (step 62). The system then compares the resulting processed patient data with the feature data (step 63). The result of this comparison operation can be a categorization indicator and a confidence value. The categorization indicator is an indication of which category the patient's joint best matches, and the confidence value is an indication of the level of confidence exhibited by the match. Also available is the underlying image comparison data.

If earlier joint data is also available, the system can derive trend information from the series of data sets (step 64). This derivation step can be part of an enhanced comparison operation in which the different joint data are processed in a single operation, or it can be a separate operation. The resulting data are then presented in a patient report (step 66), which can include a physician-readable portion, a patient-readable portion, and/or a machine-readable portion.

Based on the report, the physician, patient, and/or the system can take or refrain from taking action (step 68). Actions can include a wide variety of treatment-oriented actions including prescribing or adjusting a prescription of medication, surgery, exercise, or prosthetics. These types of actions are typically initiated by a physician or other health care practitioner, but in some cases, they may be automated. For example, a rehabilitation-oriented exercise machine may be able to adjust its resistance settings based on a patient report accessed electronically. And an implanted drug delivery system could also adjust drug delivery levels based on an electronically accessed patient report.

Other types of actions can also be taken, such as choosing to admit a patient in a clinical trial, certifying results for a clinical trial, transferring results to a database for further study, or comparing results to other types of diagnostic methods. In veterinary applications, actions might include choosing to breed an animal, selecting an animal for a particular task or training regiment, or even euthanizing an animal that cannot be treated. These types of actions will typically be performed by a health care practitioner, although they may also be automated or performed by less skilled personnel.

Figure 3:
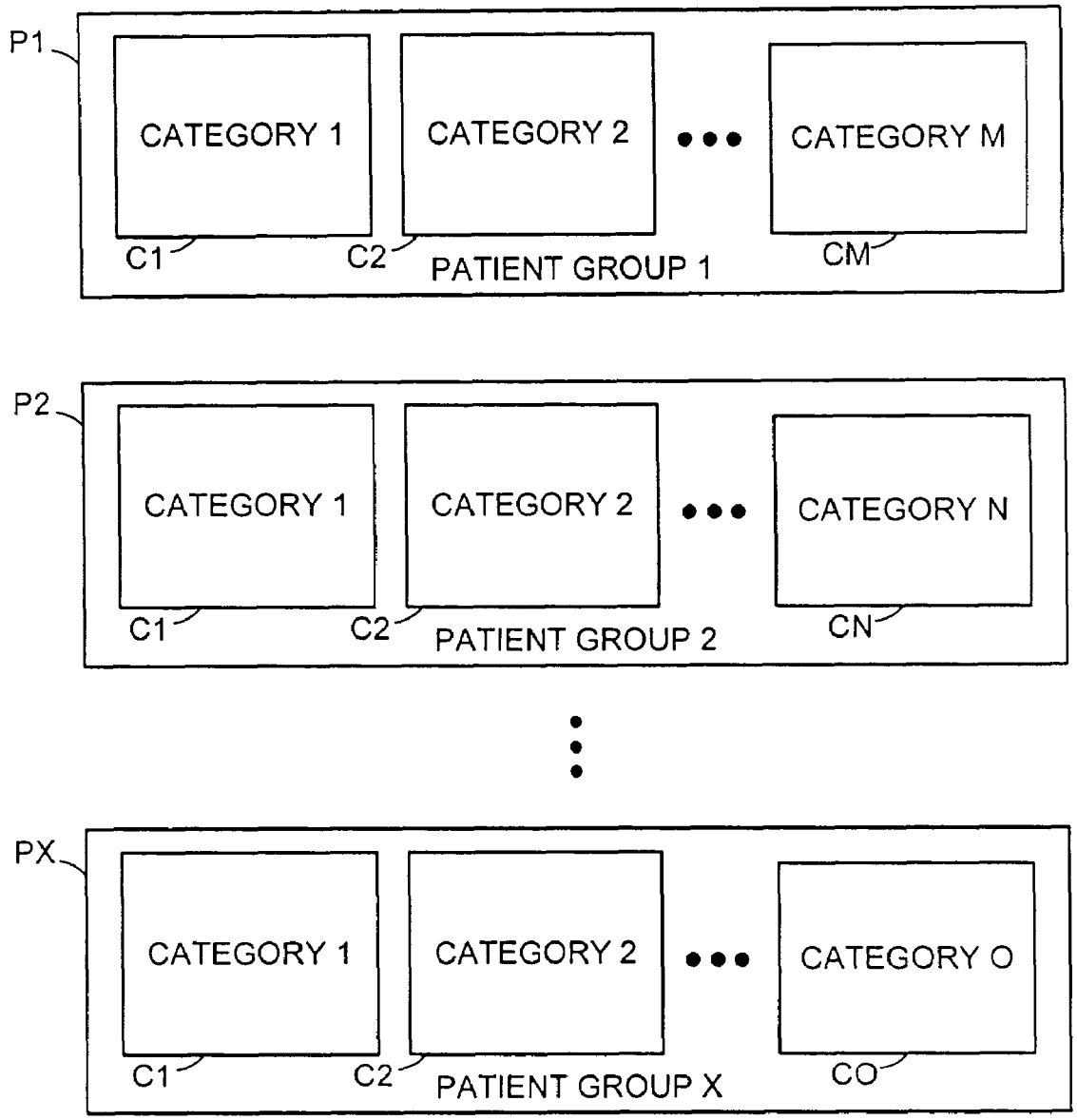
FIG. 3 is a data diagram for feature data for the system of FIG. 1.

Referring to FIG. 3, the system 10 can apply different analytical techniques to different patient populations P1, P2, . . . PX. Each of these populations may exhibit the same or different categories C1, C2, . . . CN, . . . CO. The populations may be selected based on a variety of different criteria, such as age, occupation/activity level, or a preexisting diagnosis. The categories may be derived based on particular objectives, such as the selective diagnosis of different types of joint diseases. One population of interest is that of highly trained athletes, because their intensive training regimens may result in patterns of wear that differ from the general population. The health of their joints may also benefit from more frequent screening that do members of the general population.

Figure 4:
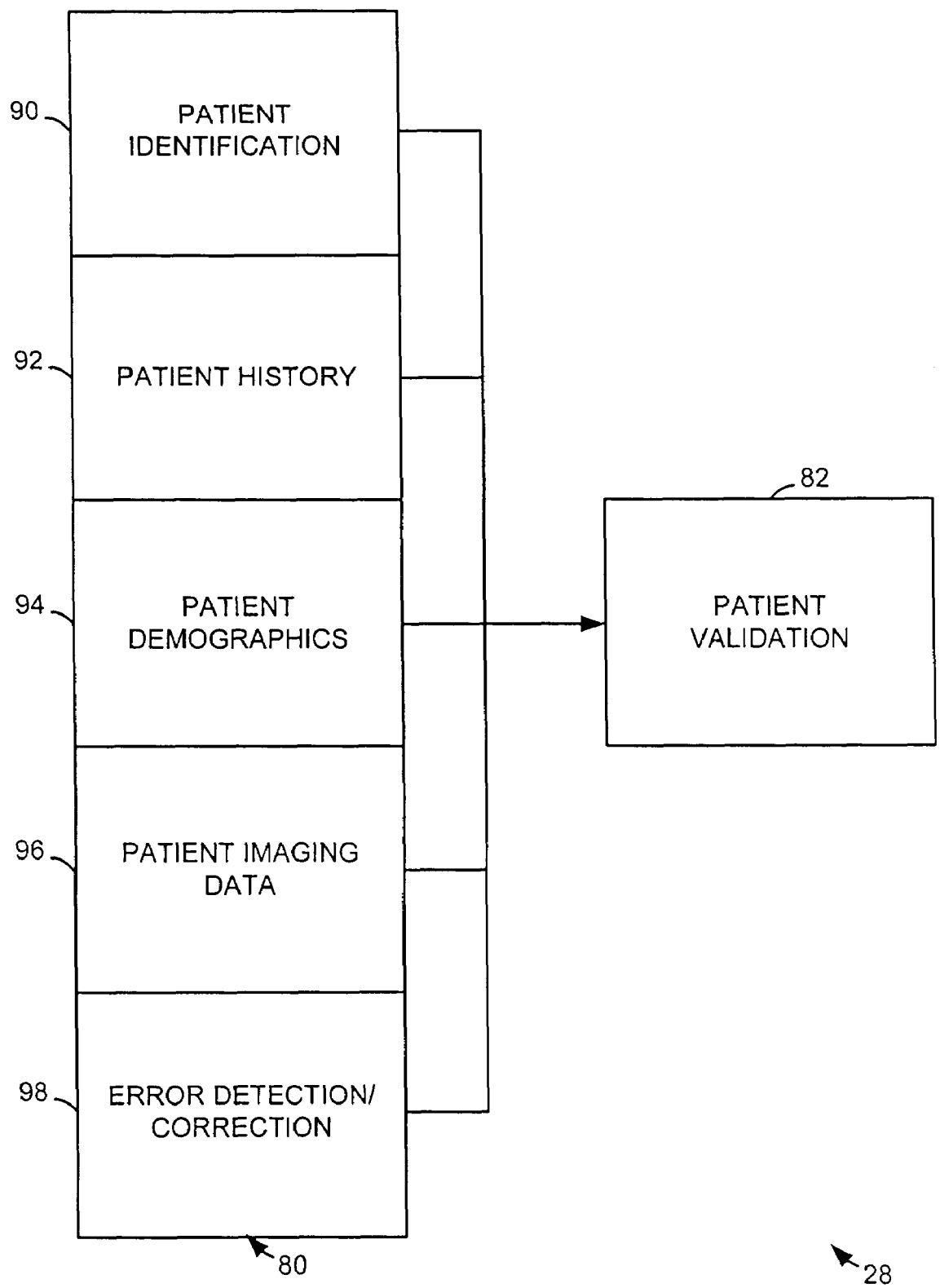
FIG. 4 is a patient record data diagram for the system of FIG. 1.

Referring to FIG. 4, the patient data storage preferably includes patient record storage 80, and patient validation logic 82. The patient record storage can include storage for patient identification information 90, such as name, address, and identification number (e.g., social security number). The patient record storage can also include storage for patient history information 92, such as prior symptom and treatment information, prior patient image data, and prior processed patient image data. The patient record storage can further include storage for patient demographic information, such as patient age, race, and occupation. The patient record storage can also include storage for patient imaging data 96, such as one or more active MRI image data files. Error correction/detection encoding 98 may be provided at the record level, or it can be provided in the underlying systems.

The patient validation logic 82 helps to avoid errors in processing patient data. To this end it checks different parts of the patient records before allowing processing on a record to ensure that the correct record or the correct part of the record is being processed. To avoid comparing the knees of different patients with the same name, for example, the validation logic can flag situations where patient names match, but identification numbers, ages, or other information does not match. Similarly, to avoid comparing one patient's left knee with his or her right knee, a knee identification field can be compared with a simple test of the image data. Although the patient validation logic 82 is particularly important in the case of some ongoing clinical applications of the system, it may not be important or even required in other applications, such as one-time screening or veterinary applications.

EXAMPLE

The following example illustrates an approach to designing a system intended to allow for the assessment and diagnosis of osteoarthrisis (OA) using MRI cartilage layer thickness measurements. Although diagnosis based on cartilage thickness progression could still be made more precise, promising results have been obtained using the concept of normal joint templates. This approach employs a normalizing procedure that allows for the comparison of patient thickness maps to normal templates. Scaled difference maps can then be generated depicting cartilage deficit with respect to the normal reference.

To enable diagnosis based on normalized thickness for a particular patient, a decision rule is defined on the basis of synthetic quantitative parameters. One possibility is to compute the fraction of articular surface for which the scaled deficit exceeds a given threshold. The pathology severity could be related to this value and classes could be defined using different fraction thresholds. The main drawback of this approach is likely to be in the loss of topographic information, which may be critical, in the diagnosis decision rule.

The system design objective in this example is to create an objective, automatic and robust classification method—based on scaled difference—that takes into account spatial information. The general approach is to identify pathology patterns classes in an OA population, and this approach may be of great interest as a patient selection step for clinical studies. The identification of a few representative cartilage wear patterns may also constitute a solid base for pathology understanding, particularly if correlated with other indicators such as joint kinetic moments or meniscus tear scoring.

Signal classification is a known technique in "hard science" fields such as artificial intelligence, pattern recognition, computer vision, or statistical analysis. It can be decomposed in three main tasks: feature extraction, feature-based class definition and finally feature classification. In the present case, given that classes are not defined a priori, the problem is known as an unsupervised classification problem.

Feature definition has a strong influence on class definition and final classification. Because no trusted and explicit (parametrical, geometrical or anatomical) criterion were available for feature selection, it was decided to use a general feature definition based on information theory and statistical analysis. A basic framework consists of following steps:

image information compression, keeping meaningful data structures using methods such as principal component analysis (PCA), factor analysis (FA), or independent component analysis (ICA)

image classification in the reduced space (with supervised or unsupervised methods, that may or may not use underlying probabilistic models)

A simple classification procedure based on PCA and K means algorithm for clustering was tested. It is noted that this approach does not rely on an explicit underlying data model, but such a model could be derived through statistical non-linear mixture modeling.

Femoral cartilage thickness maps of 110 OA patients and 10 normal age-matched patients were first processed from cartilage interface contours segmented with a semi-automatic method, as presented in U.S. Pat. No. 6,560,476, discussed above. The maps employed a cylindrical parameter space using a fitted cylinder as a primitive. A normal thickness template was first generated by aligning, scaling and averaging the maps for the 10 non-arthritic subjects (see FIGS. 9-10).

Figure 6:
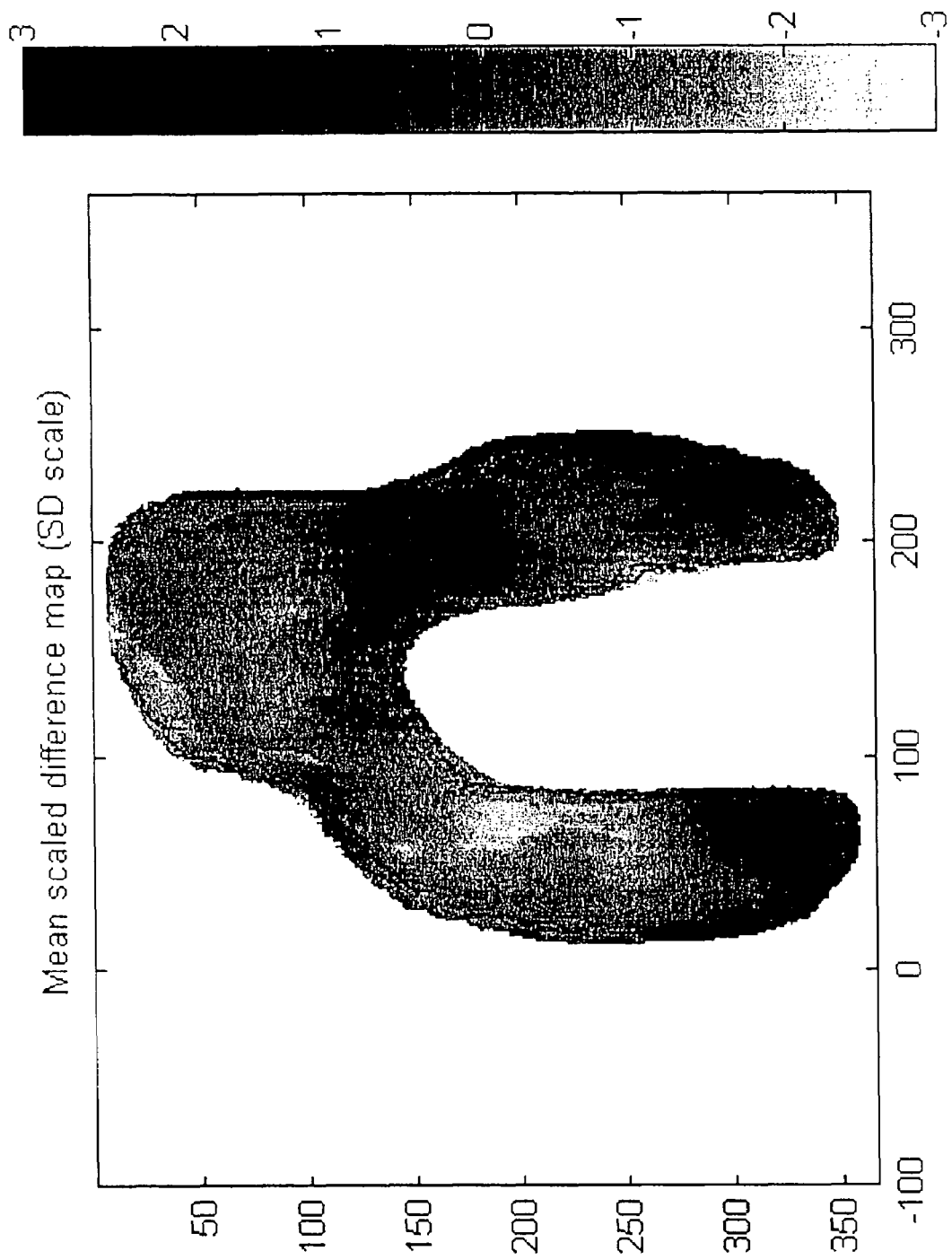
FIG. 6 is a plot of the mean of scaled difference maps of members of an OA population (110 subjects)

Scaled difference maps could then be generated by subtracting patient OA maps from the normal template and scaling the resulting difference by a standard deviation (SD) template. Referring to FIG. 6, for example, a map of mean scaled differences among members of an OA population of 110 subjects shows average deficit and surplus cartilage thickness in a the population. Medial condyle (left) and trochlea regions show clearly a significant deficit ($>=3$ SD) whereas other regions are not significantly thicker than normal.

To simplify computations, patient surface scaling and alignment were applied directly in the parameter space. Five different alignment and scaling methods have been evaluated, and their main characteristics are summarized in Table 1. The first four methods share the same principle: alignment of map bounding box centers, surface matching by uniform and linear scaling on the two parameter dimensions, bicubic thickness interpolation, and, finally, thickness scaling using the same factor as the one used for surface matching. The methods differ in the way the scaling factor is estimated: map anterio-posterio hight (AP), map medial-lateral width (ML), fitted cylinder radius (R), and cartilage surface square-root (SSR).

TABLE 1

Summary of alignment and scaling methods

| | Alignment | Surface scaling | Thickness interpolation | Thickness scaling |
|---|---|---|---|---|
| Method 1 | Alignment of the maps bounding box centers | Uniform scaling along the two parameter dimensions using the anterior-posterior height of the map as the scaling factor (AP) | Bicubic interpolation in the parameter space | Normalization of thickness values by the scaling factor. |
| Method 2 | | Same procedure using the map medial-lateral width as the scale factor (ML) | | |
| Method 3 | | Same procedure using the fitted cylinder radius as the scale factor (R). | | |
| Method 4 | | Same procedure using the surface square root as the scale factor (SSR). | | |
| Method 5 | Biquadratic surface warping based on feature points extracted from map contours. | | | Surface square root scaling factor (SAF) |

Figure 5:
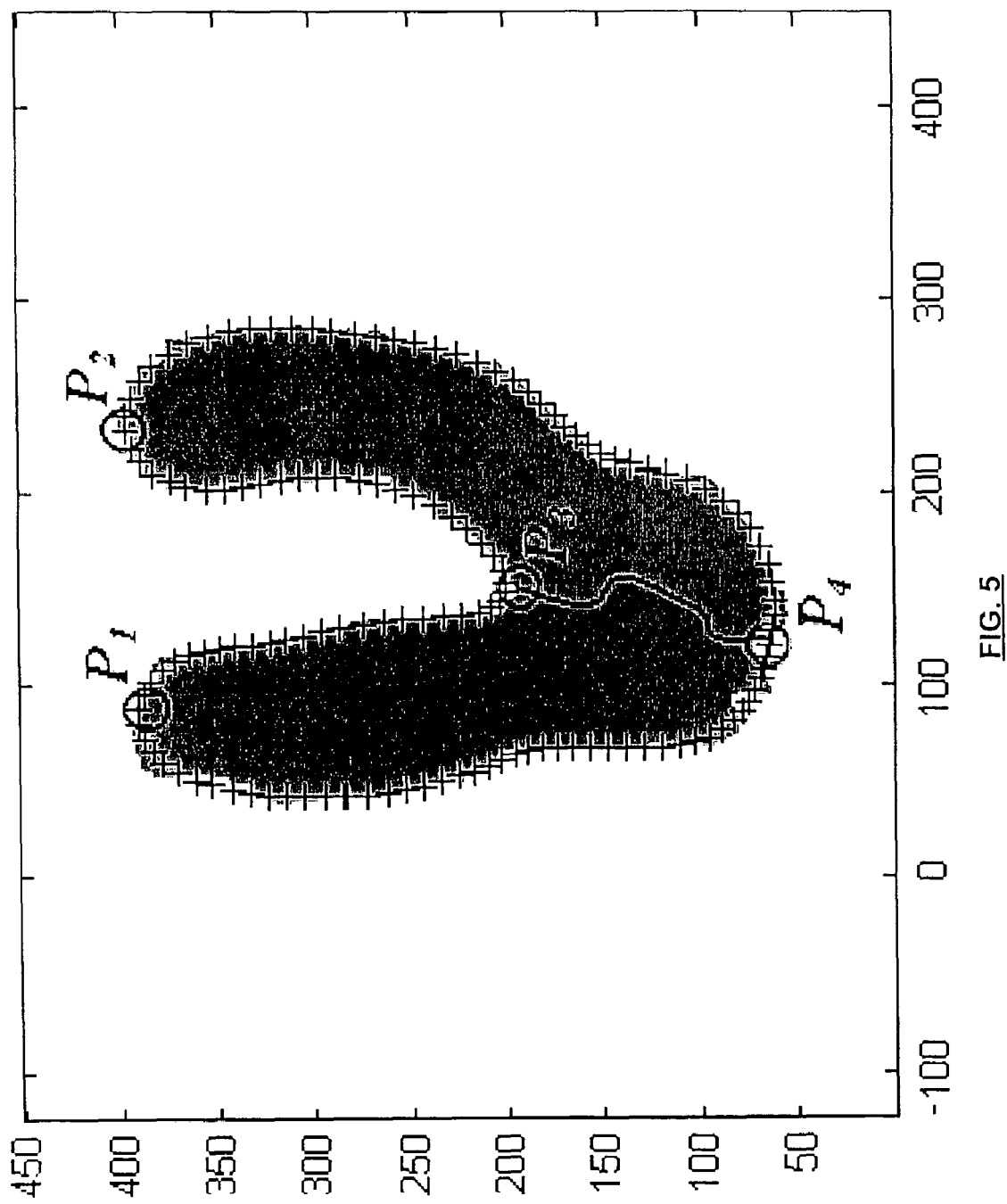
FIG. 5 is a cartilage diagram illustrating the definition of the first four feature points on a femur map for the system of FIG. 1.

The last method is a warping method based on feature points extracted from the map contours. Four anatomical points P1-P4 are first defined on the femur map as shown in FIG. 5. P1 and P2 are the local maxima points on the condyle parts, and P3 is the local minimum in between. P4 is the intersection between the bottom contour and the Blumensat line.

Other feature points are defined by equal subdvision of the contour sections defined by the anatomical features. Averaging these features among all the subjects defines the reference features. A biquadratic transformation is estimated for each subject to transform subject features to reference features. This transformation is then used to process the matched thickness maps. Finally, as for former methods, a scaling factor (equal to the surface square root ratio) is applied uniformly to thickness values.

The classification method provides an objective and topographical base for the pathology map class definition. Given the high dimension of data (each map contains typically 50000 points) and the great variety of scaled difference map topographies, information should be simplified and summarized (compressed or coded) to extract only the most significant patterns. Hence, feature definition and extraction is the first step for map (i.e., signal) classification. There is no explicit and objective formulation of these features because pathology classes are not defined. Yet, it seems likely that classes will rely on wear region pattern characteristics, including the number of regions, their positions, and their topographic properties.

One way to bypass explicit feature definition is to consider maps as signals and features as the uncorrelated information they contain. From this point of view, feature extraction is seen as a signal quantization process.

In this example, it was decided to follow a classical framework used in multivariate data analysis and information theory. Each map is viewed as a multi-dimensional set of variables. Information is first reduced exploiting linear correlation via principal component analysis (PCA), and then classes are defined using an unsupervised classification method applied on uncorrelated coefficients. PCA is actually an appropriate tool to code and decorrelate difference map information. It will naturally associate correlated zones and constitute an optimal base to automatically define variation classes. Class definition using PCA is optimal in the sense that classes best represent (relative to a chosen inter-map distance measure) the variance of the reference maps.

PCA application to image analysis has been successfully used in the computer vision field for face recognition. In this application, maps are considered as 2D images in a M×N dimension space. Each image of this space can be represented by column vector of length d=M.N, which is simply the lexicographic reading of that image. The result is an d-dimensional space, called map space, in which wear patterns can be characterized.

Figure 7:
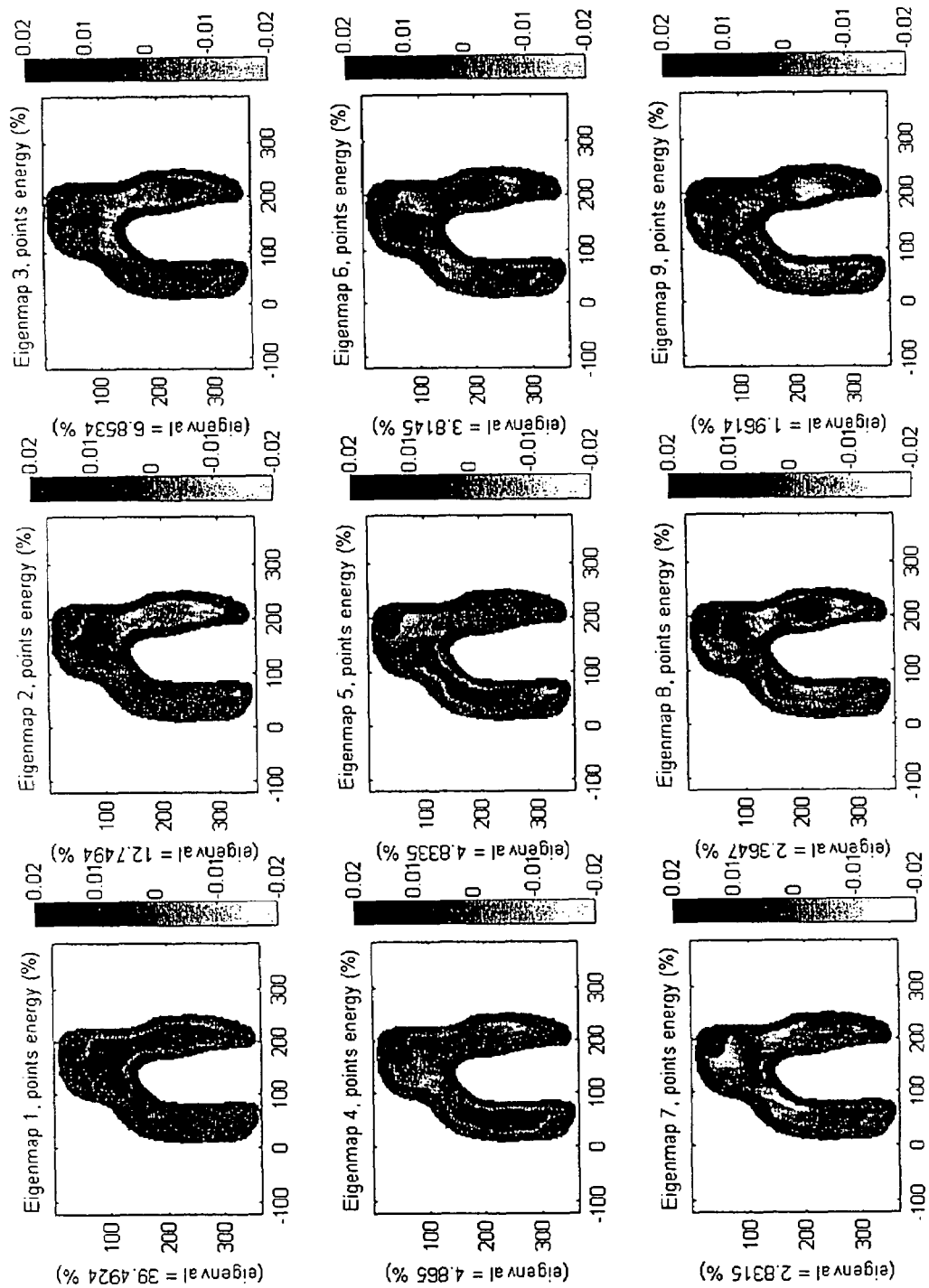
FIG. 7 presents a series of plots showing the first nine most significant eigenmaps computed from 110 subjects in scaled difference map space (energy contribution in percentage points), in decreasing importance order.

Referring to FIG. 7, a typical set of thickness scaled difference maps can be chosen as a reference to describe the variety of pathology cases. The PCA procedure defines a sub-space that contains the most significant information (i.e., variations around an average map) from the reference maps, automatically associating correlated map points, in order to build few typical base maps (eigenmaps) mostly representative of the main variations of the reference maps. Each reference map can then be represented, in a simplified way, as a linear combination (eigenmap components) of few eigenmaps. Only the main information is retained.

In mathematical terms, an eigenspace is spaned by an orthogonal base of eigenmaps defined as the eigenvectors of the correlation matrix of the reference signals. Eigenmap components are defined as the projection of the reference maps onto the eigenmaps. Eigenvectors are built orthogonally one to each other, which means eigenmap components are uncorrelated. They also maximise the variance of eigenmap components. Each eigenmap is associated to an eigenvalue proportionnal to the information quantity it contains.

Let T be the (d×q) matrix containing q reference maps represented as (d×1) column vectors $t_i$. In fact, PCA provides a geometrical solution to approximate each $t_i$ by its orthogonal projection ($\hat{t}_i$) in a sub-space. This sub-space, spanned by (d×q) orthogonal matrix A, is chosen to maximize variance of ti components in it. In order to satisfy maximal variance property, A is composed of the q most significant eigenvectors (eigenmaps) of the correlation matrix C of T ($C=(T-\bar{T}).(T-\bar{T})^T$). Let μ be the mean reference maps. $\hat{t}_i$ can then be written as, $$\hat{t}_i = AA^T(t_i-\mu)+\mu$$

Defining (q×1) vectors $s_i$ (eigenmap components) as the components of the maps in the eigenspace, we have, $$s_i=A^T(t_i-\mu) \text{ and } \hat{t}_i=As_i+\mu$$

Moreover, defining the reconstruction error vector $\epsilon_i$ as:

$$\epsilon_i = t_i - \hat{t}_i$$

In other words, PCA provides a linear model for original data:

$$t_i = As_i + \mu + \epsilon_i$$

Data can even be more compressed by selecting only the q' most significant eigenvectors. (q×q') matrix $A'_i$, with q'<q, replaces matrix A.

Given the nature of wear process, data points have been observed to be highly spatially correlated. Most of maps show large regions where the signal can be approximated by a linear model. In other words, the signal is not highly textured and does not appear to need higher-order moment data models. Moreover, as far as diagnostic and classification are concerned, constant mean region patterns are sought and it is expected that PCA will simplify information and highlight these patterns. Many non-linear PCA extensions have been designed (probabilistic PCA, ICA . . . ) for other applications but it is not clear that they are necessary the present type of signal and issue.

Figure 8B:
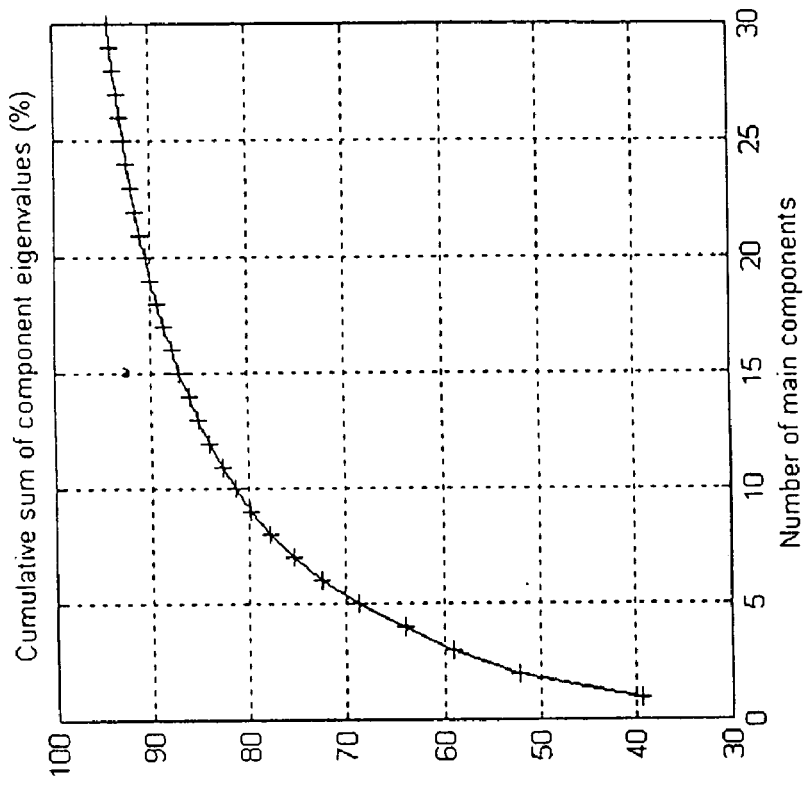
FIG. 8 includes a pair of plots showing information distribution among components for the eigenmap series of FIG. 7.
Figure 8A:
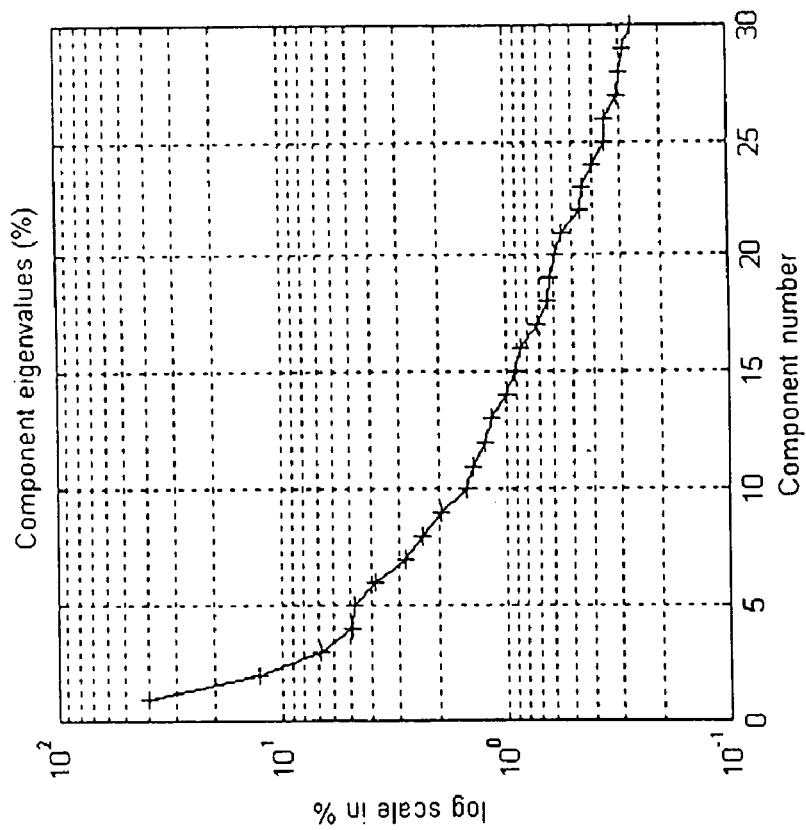

Eigenmaps represent population variations along an associated axis of the average map. They are shown in FIG. 7 in decreasing order of variation importance. To each eigenmap is associated an eigenvalue that is equal to the standard deviation of the map population projected on the variation axis. Eigenvalues are propotionnal to the quantity of information the eigenmap can represent. Their "representativeness" is expressed in percentage points in FIG. 7. FIG. 8 shows information distribution among the thirty main components. The right plot represents the cumulative information they retain. Hence it is noted that the ten first components represent more then 80% of the information.

The first eigenmaps can describe great variations (large zones and/or high variation amplitude). The latest ones allow the system to model smaller details (small zones and/or low amplitude variations). The observable patterns or structures (groups of connex points having roughly the same value) represent thinner (or thicker) zones that allow to describe the most different maps. Given the nature of the map population signal, eigenmaps show simple and regular patterns like homogenous regions. Note that region sizes decrease with the component representativeness. In other words, selecting a restricted number of components allows to generate maps with a certain "spatial resolution". The more components used, the smaller is the spatial resolution. This property will be considered for selecting the number of classification components.

Contrary to supervised classification cases, class definition is not treated as available in this case. Some clinical features, such as meniscus tear score or pain test results, could be used for classification, but the goal of the method is actually to propose a way to define classes on the base of quantitative cartilage thickness information.

The general concept of class definition raises the following questions:
How to decide when data variations are intra-class variability or inter-class variability
Variability definition itself raises the question of how to define distances between individuals and more generally how to model data In this case, data variations are caused by both spatial structure variability (point correlation variations) and point intensity variability. A map class modeling was defined in order to adequately describe these variations in terms of intra-class and inter-class variability.

The PCA compression step already assesses an implicit constraint on class definition because orthogonal projection eradicates the smallest data variations, in the sense of Euclidian distance between signals. The choice of the projection does not guarantee that compression is optimal in terms of classification performance. In contrast, methods using an a priori class definition, on a training set, can explicitly optimize projection axes so that inter-class variability is maximized (discriminant analysis).

The K-means algorithm was initially chosen in the map space because of its simplicity and efficiency. K-means is simple and powerful clustering algorithm that minimizes the average intra-class distance also called quantization error E. In other words, for a set of N eigenmap component vectors $s_i$, K-mean defines M class centers $\omega_k$ that minimize E(ω):

$$E(\omega) = \sum_i \frac{1}{2} \min_k [dist(s_i, \omega_k)],$$

where $dist(s_i, \omega^k) = (s_i - \omega_k)^2$ in the Euclidian case.

The choice of Euclidian distance implies that classes have hyper-spheroid shapes. Other distance types like Malhanobis or generalized distance also exist allowing for seeking of hyper-ellipsoid and probabilistic shapes. Given the absence of specific knowledge about the class shapes, the Euclidian distance was chosen because of stability results. A combination of batch and on-line versions of the algorithm were used in order to optimize convergence speed and accuracy.

Once classes have been defined on the training set, a new map can be simply classified by projecting it into the map space and labeling it with class that is the closest to it, using Euclidian distance.

The method needs mainly the selection of two parameters: the number of significant components and the number of classes. Many different methods can be found in the litterature to select the optimal values, depending on the data model (Gaussian mixture, geometrical . . . ) and optimization criterion (MAP, ML, ratio intra-inter class distance . . . ). Some methods using comparison with simulated reference populations (GAP statistics) have also recently been proposed, but experimental results did not appear to be well adapted to the problem at hand.

Practically, the first parameter is not critical and can be heuristicaly assimilated to the detail level at which maps are coded before clustering step. The more components are selected, the smaller and less correlated will be the reconstruction error. On the other hand if the detail level is too high, the clustering step stability will decrease and class definition will be less significant. Initially the choice to use the 10 first principal components was made heuristically on the base of information quantity (@ 80% of total variance) and pattern detail level presumed to be relevant for pathology class definition. Beginning with a small number of components then allows for a preliminary low resolution classification that describes large-scale tendencies in a robust way.

The second parameter is more complex to optimize. The main pragmatic criteria were stability and robustness towards segmentation (human factor) and clustering (influence of initialization step) variabilities. A relatively homogenous mixture proportion is also important. Clusters with very few members are undesirable. Given these considerations five clusters were used for final classification results of the example population.

Results

A normal template has been generated using 10 non-arthritic subjects. This population is relatively small because it was found to be important to select subjects in order to match normal population and OA population ages, but it should be straightforward to perform repeat studies for normal templates based on larger populations.

Figure 9:
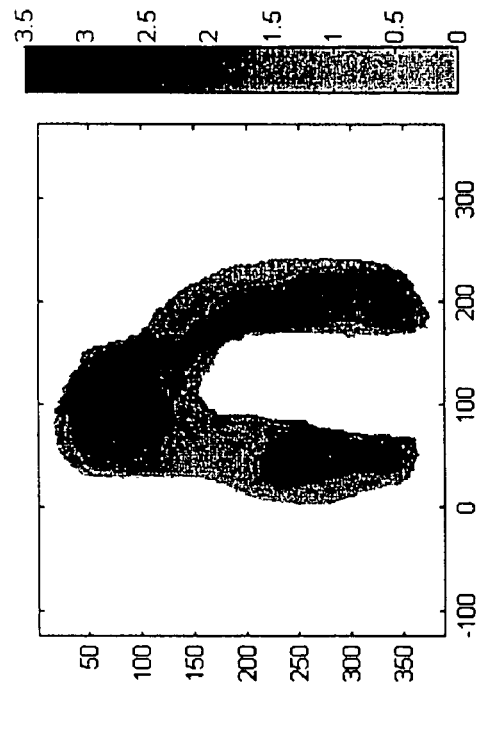
FIG. 9 presents mean cartilage thickness maps for 10 non-arthritic age-matched subjects using methods one to four in lexicographic order, with a mm scale.
Figure 9:
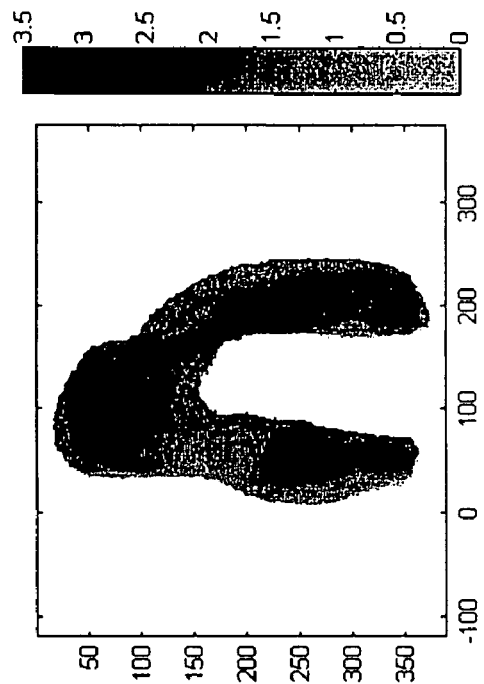
Figure 9:
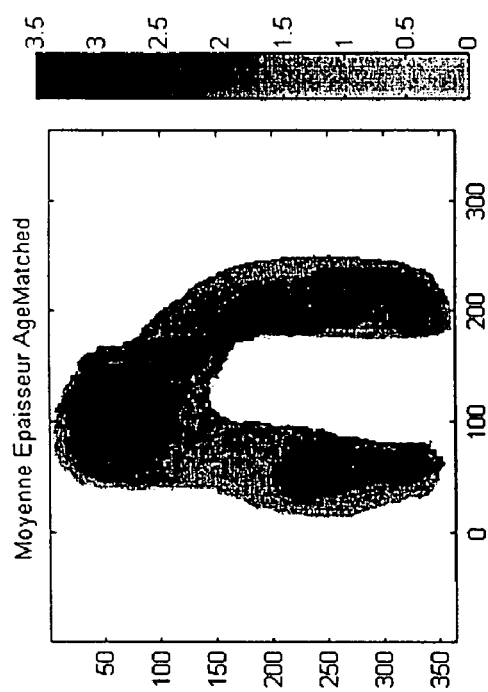
Figure 9:
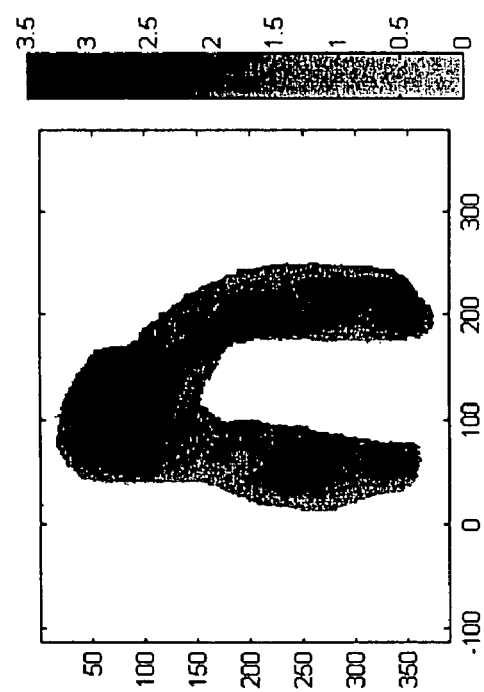
Figure 10:
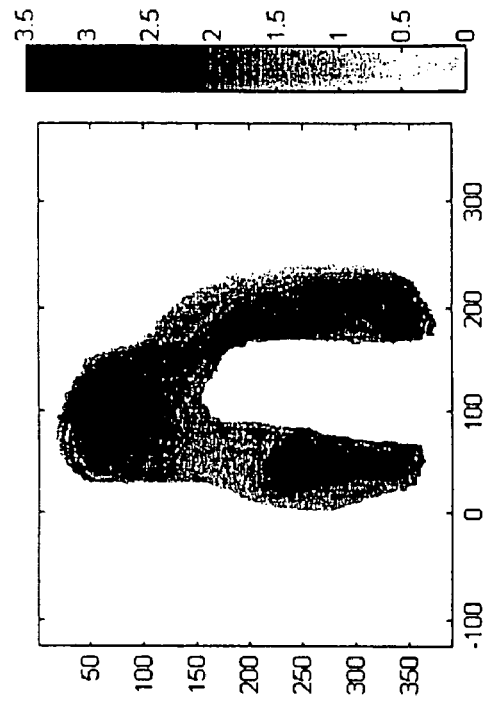
FIG. 10 presents standard deviation of cartilage thickness maps for 10 non-arthritic age-matched subjects using methods one to four in lexicographic order, with a mm scale.
Figure 10:
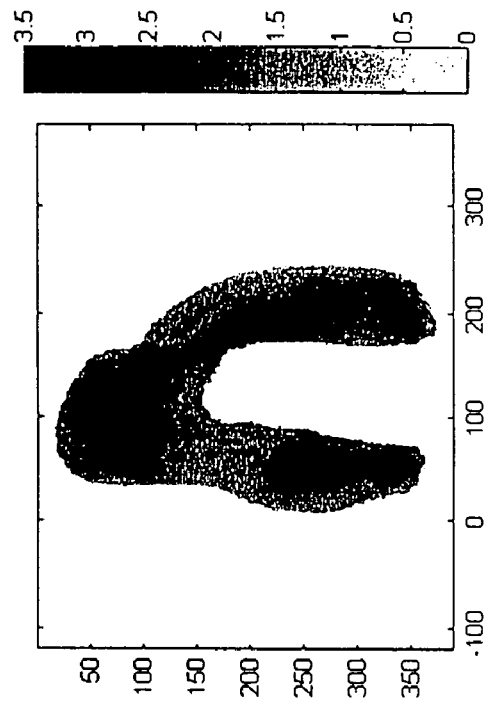
Figure 10:
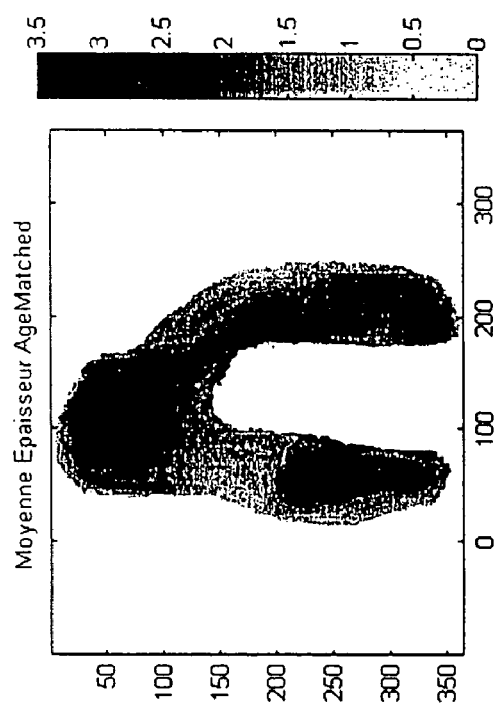
Figure 10:
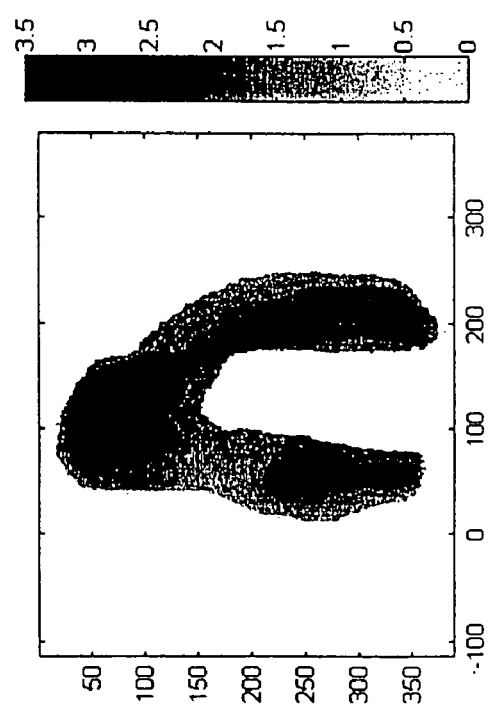
Figure 12:
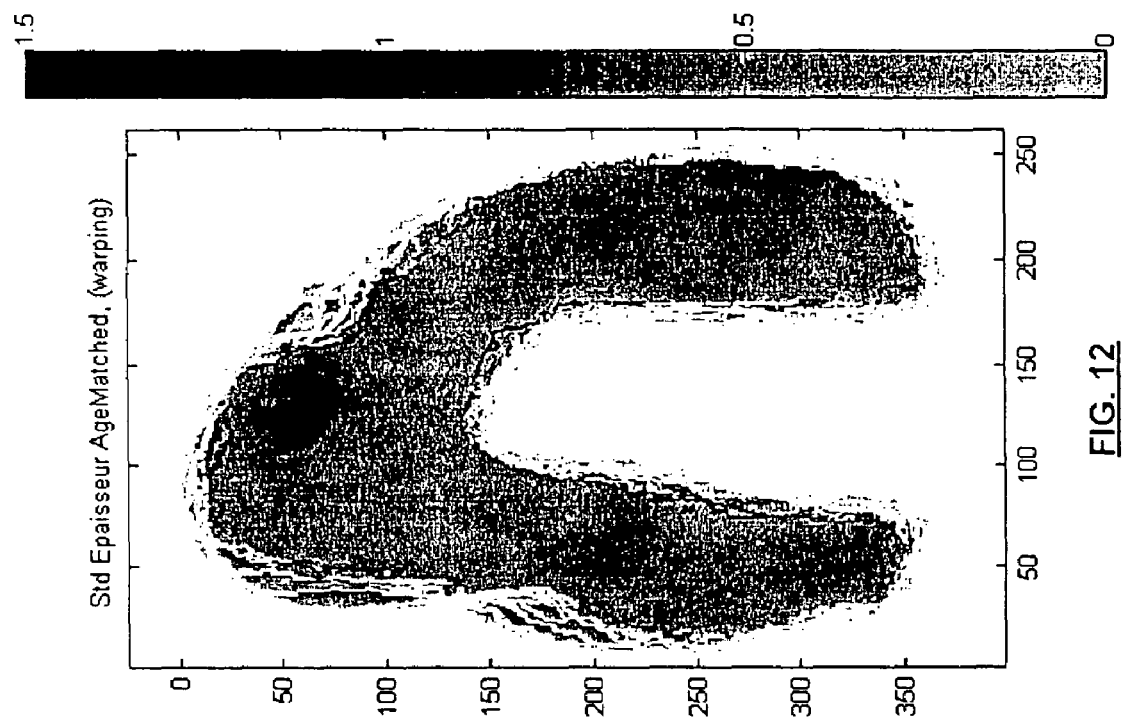
FIG. 12 presents a map of standard deviation of cartilage thickness for 10 non-arthritic age-matched subjects using a warping method (method five) in lexicographic order, with a mm scale.
Figure 11:
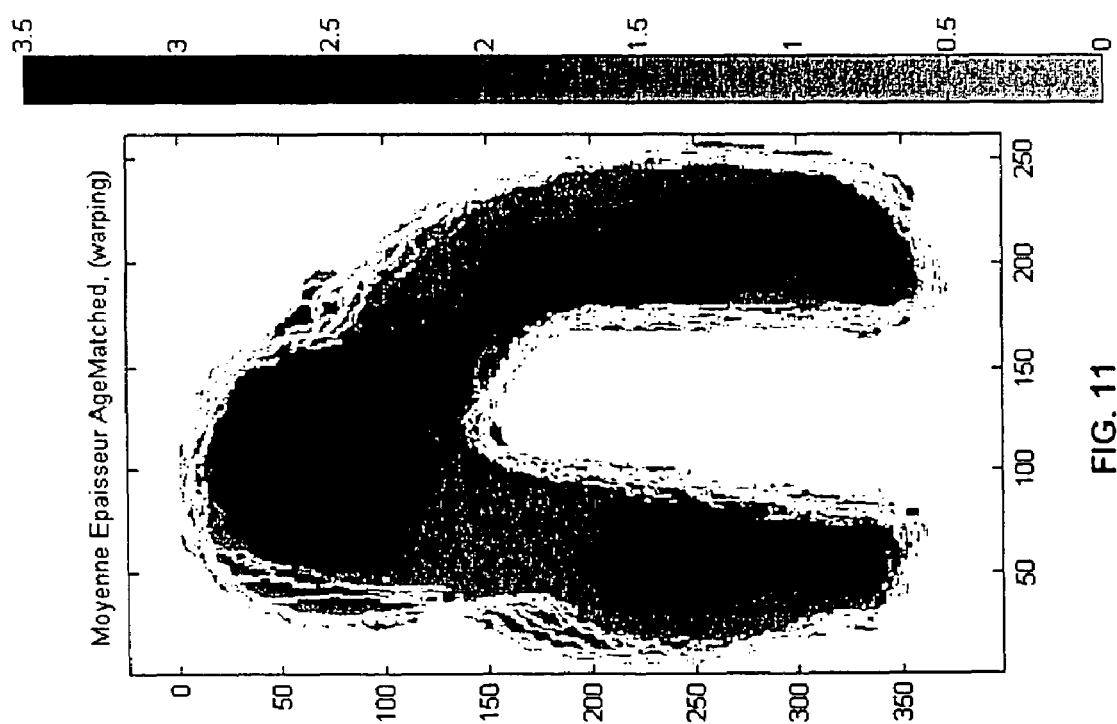
FIG. 11 presents a map of mean deviation of cartilage thickness for 10 non-arthritic age-matched subjects using a warping method (method five) in lexicographic order, with a mm scale.

Refering to FIGS. 9 and 10, template thickness mean (FIG. 9) is relatively independent of the scaling method, but this is not the case for the standard deviation (SD) of mean surface and thickness map (FIG. 10). Sum of root-mean-square of standard deviation (SD-rms) is used as an indicator of scaling factor adequacy (see Table 2 and Table 3). It was noted in preliminary studies that SD-rms is very much dependant on the number of maps used to compute a template. Because anterior-posterior scaling factor (AP) gave relatively good results for different populations and because it was refered as a pertinent scaling method in the literature, it was selected for use in the following steps.

TABLE 2

|  | Method 1 (AP) | Method 2 (ML) | Method 3 (R) | Method 4 (SSR) |
| --- | --- | --- | --- | --- |
| Thickness SD rms (mm) | 2.7240 | 2.8689 | 2.7668 | 2.5516 |
| Thickness CV rms (%) | 11.0252 | 11.4131 | 10.9338 | 10.3995 |

Table 2 presents root-mean-square of cartilage offset standard deviation and coefficient of variation for 10 normal age-matched femurs using four different scaling methods. In the table, AP stands for anterior-posterior, ML stands for medial-lateral, R stands for radius of fitted cylinder, and SSR stands for surface square root.

TABLE 3

|  | Method 1 (AP) | Method 2 (ML) | Method 3 (R) | Method 4 (SSR) |
| --- | --- | --- | --- | --- |
| Thickness SD rms (mm) | 0.4151 | 0.4009 | 0.4400 | 0.4071 |
| Thickness CV rms (%) | 24.4235 | 23.7568 | 25.5213 | 23.8798 |

Table 3 presents root-mean-square of cartilage thickness standard deviation and coefficient of variation for 10 normal age-matched femurs using four different scaling methods. In the table, AP stands for anterior-posterior, ML stands for medial-lateral, R stands for radius of fitted cylinder, and SSR stands for surface square root.

Figure 13:
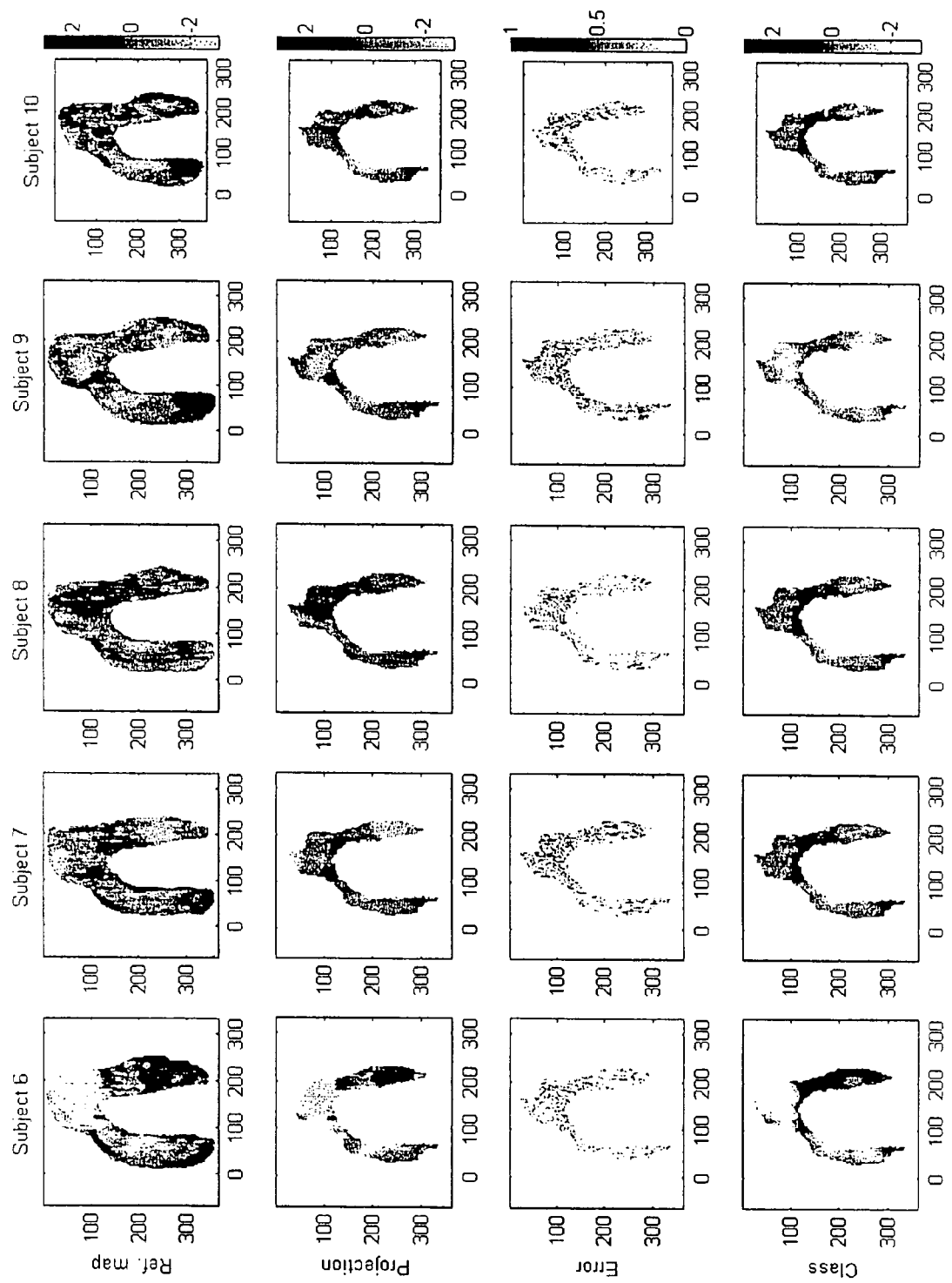
FIG. 13 presents a series of eigenmap space results for subjects 1 to 5 (columns) for, in rows one to four, reference map (scaled difference), projection in the eigenspace using 10 components, reconstruction error, and associated class map (6 classes)
Figure 14:
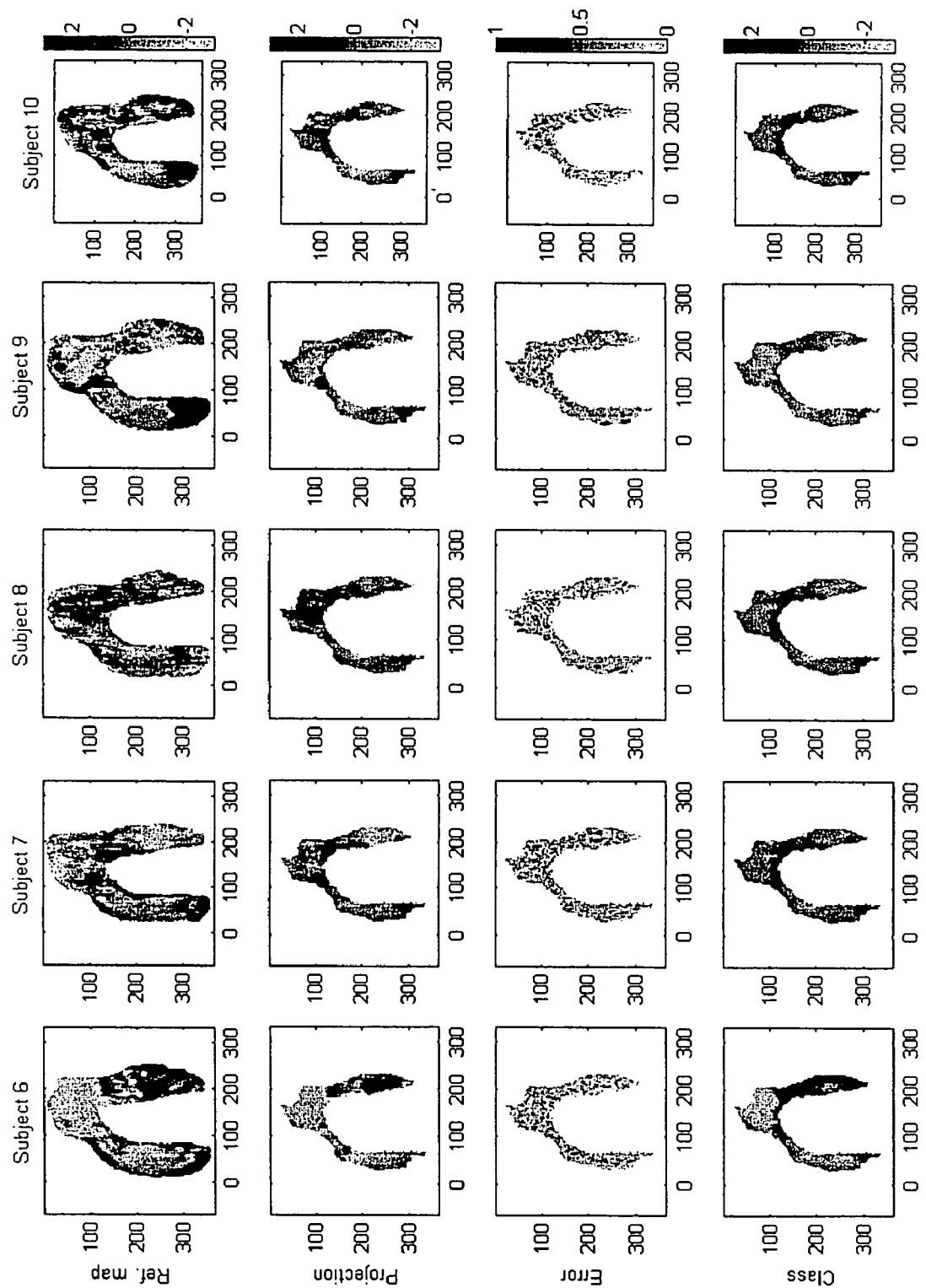
FIG. 14 presents eigenmap space results for subjects 6 to 10 (columns) for, in rows one to four, reference map (scaled difference), projection in the eigenspace using 10 components, reconstruction error, and associated class map (6 classes)

Eigenmaps have been computed using baseline acquisition of 110 OA subjects normalized by a template based on 10 non-arthritic subjects. All maps have been projected in the eigenspace and reconstructed in the full dimension space. As an indication, FIGS. 13 and 14 show results for subjects 1 to 5 (columns, FIG. 13) and subjects 6 to 10 (columns, FIG. 14). Rows show reference map (scaled difference), projection in the eigenspace using 10 components, reconstruction error and associated class map (6 classes).

Projected maps are very similar to the original ones. The error information for each subject is relatively uncorrelated, which means that 10 components are sufficient to capture original signal structures relatively well. Finally it is noted visually that original global map structures are very similar to the ones present in the class map they have been assigned to. Classes therefore visually represent the main features of the signal well.

Three type of results have been generated:
  baseline and follow-up classification comparaison
  meniscus tear scoring and classification dependancy analysis
  subjet gender and and classification dependancy analysis Baseline and follow-up classifications have been carried out as a preliminary test to evaluate the consistency over time of classification changes. It is expected that the method will filter segmentation noise and provide a more significant general cartilage change indicator. Dependency between clinical features like meniscus tear score or subject gender allows the evaluation of class labeling consistency from a pathological point of view.

Figure 15:
FIG. 15 presents scaled difference maps of five clustered classes and their a posteriori probabilities for base line cartilage surfaces, with the medial side corresponding to the left part of the map.
Figure 15:
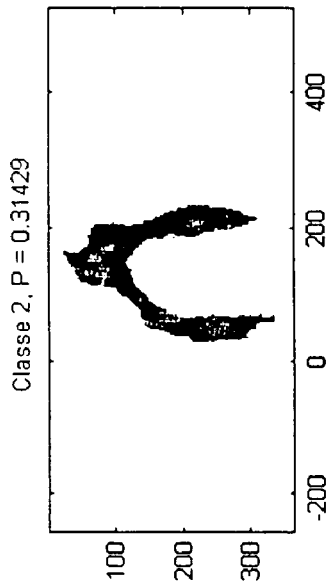
Figure 15:
Figure 15:
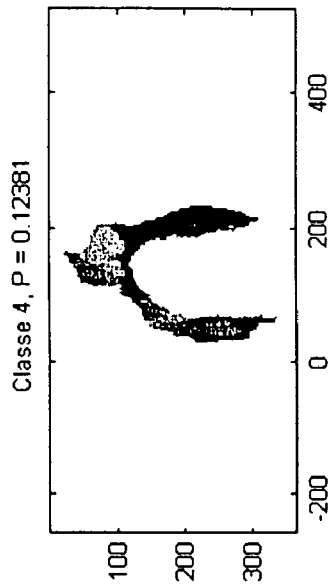
Figure 15:
Figure 15:
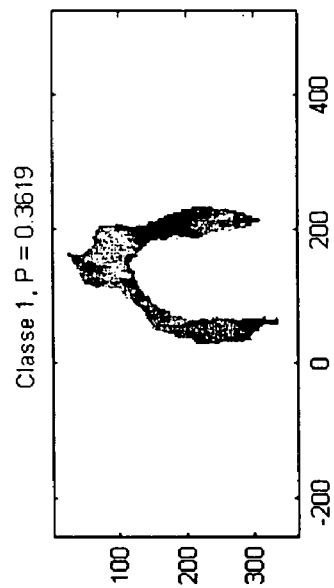
Figure 15:
Figure 15:
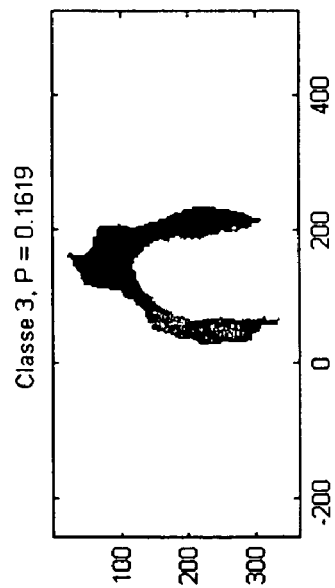
Figure 15:
Figure 15:
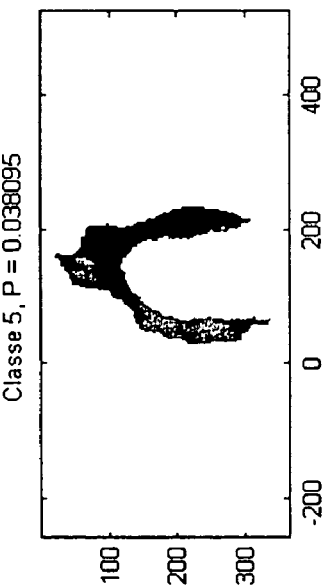

FIG. 15 presents scaled baseline difference maps of the five classes clustered by the K-means algorithm applied on 105 OA patients for which follow-up was available. Class a posteriori probabilities of the classes were computed. These class maps could qualitatively be interpreted as follows:
  Class 1: global significant cartilage loss
  Class 2: global cartilage loss tendancy
  Class 3: medial condyle significant loss, medial trochlea loss tendancy
  Class 4: medial condyle significant loss, trochlea significant loss and medial condyle loss tendancy
  Class 5: very similar to class 3

Table 4 and Table 5 present scaled difference map classification probability evolution from base line to follow-up. Follow-up scaled different maps are classified in the eigenspace by minimizing Euclidian distances to the baseline class centroids.

Table 5 shows the class probability for baseline and follow-up. The main change seen is that patients for class C2 moved to class C1 which corresponds to a general cartilage loss. Table 4 presents classification transitions and their occurrences. Corresponding cartilage evolution is also listed. Note that 96 out of 105 are stationary, eight transitions correspond to a cartilage loss and only one reflects cartilage gain.

TABLE 4

|  | $P(C_1)$ | $P(C_2)$ | $P(C_3)$ | $P(C_4)$ | $P(C_5)$ |
| --- | --- | --- | --- | --- | --- |
| Base Line | 0.3619 | 0.3143 | 0.1619 | 0.1238 | 0.0381 |
| Follow-up | 0.4095 | 0.2762 | 0.1524 | 0.1333 | 0.0286 |

TABLE 5

| Base Line Classification | Follow-up Classification | Cartilage evolution | Occurences |
|---|---|---|---|
| Classe i | Classe I | stationary | 96 |
| Classe 2 | Classe 1 | general loss | 5 |
| Classe 3 | Classe 2 | light lateral loss | 1 |
| Classe 3 | Classe 4 | medial and trochlea loss | 1 |
| Classe 4 | Classe 3 | medial and trochlea gain | 1 |
| Classe 5 | Classe 4 | medial and trochlea loss | 1 |
| | | | =105 |

Figure 16A:
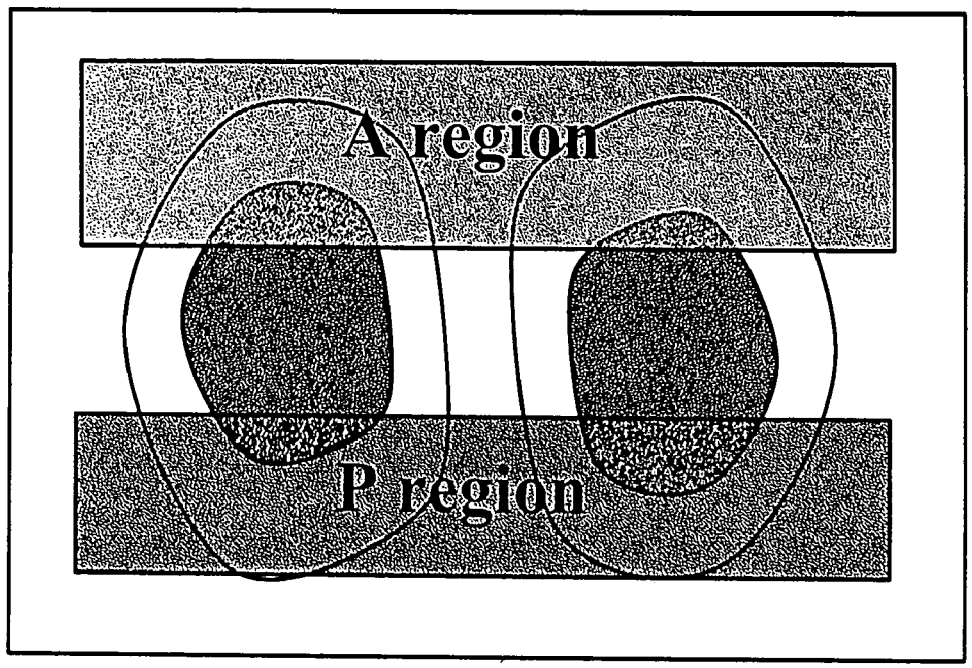
FIG. 16 is a diagram presenting four major regions for use in capturing possible lateral or longitudinal gait tilt tendencies.
Figure 16B:
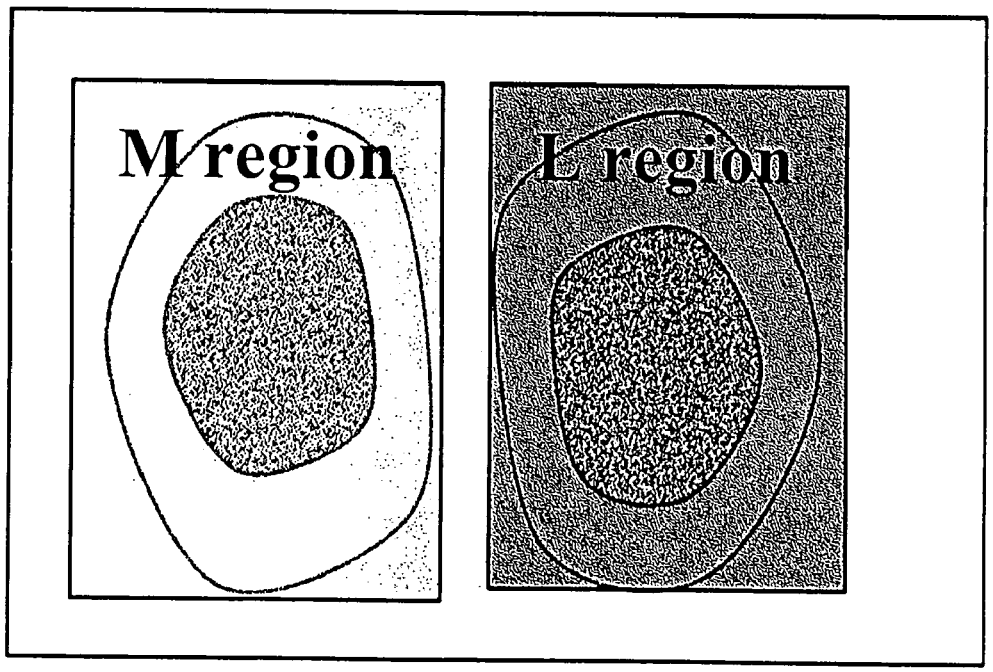

Meniscus tear scoring was carried out for each patient. Using a combination of anterior/posterior (anterior, medium, and posterior positions) and lateral/medial (lateral and medial position) axes, six meniscus regions were defined (lateral region codes: AL, ML, PL; medial region codes: AM, MM, PM). Each region was scored by a binary tear score (1=tear, 0=no tear). In order to simplify and filter information, data was summed up in four major regions (medial, lateral, anterior, posterior coded M, L, A and P—see FIGS. 16A and 16B). Major region scores were computed heuristically as follows in order to capture possible lateral or longitudinal gait tilt tendencies:

M=1 if AM+MM+PM>1, else M=0
L=1 if AL+ML+PL>1, else L=0
A=1 if AM+AL>1, else A=0
P=1 if PM+PL>1, else P=0

Tear conditional probabilities of major regions were evaluated a posteriori for the four more significant classes (see Table 6). Probabilities were analyzed in order to detect rough tilt tendencies. Results are therefore compared by pairs to evaluate tilt along longitudinal (region A vs. region P) and lateral (region M, region L) axis. Intuitively, it would be roughly expected that a high tear conditional probability in a specific region relative to its paired region should have an impact on the class map topography. For example, high tear probability in the medial compartment (M region) associated with a lower probability in the lateral compartment for a given class should be associated with larger and deeper wear patterns in the medial region for a corresponding class map. Because wear processes follow a complex and multifactorial evolution, this semi-qualitative analysis has been used very carefully as a classification coherence indication.

TABLE 6

| | Tilt axis: | | | |
|---|---|---|---|---|
| | Lateral | | Longitudinal | |
| | Tear location: | | | |
| | Medial (M) | Lateral (L) | Anterior (A) | Posterior (P) |
| P(tear) | 0.5238 | 0.5429 | 0.3810 | 0.4000 |
| P(tear/$C_1$) | 0.3421 | 0.6316 | 0.1842 | 0.4737 |
| P(tear/$C_2$) | 0.5152 | 0.4545 | 0.4242 | 0.3636 |
| P(tear/$C_3$) | 0.7647 | 0.5294 | 0.6471 | 0.2941 |
| P(tear/$C_4$) | 0.6154 | 0.6154 | 0.5385 | 0.4615 |

Lateral (0.5238 vs. 0.5238) and longitudinal (0.3810 vs. 0.4) tear probabilities for the whole population are relatively balanced. Medial tear probability for class C1 (0.3421) is smaller than the lateral one in that region (0.6316). Along the other axis, posterior probability is higher than the anterior one. Class C2 is relatively balanced for both axes. Class C3 is much more unbalanced in both axes (higher medial and anterior tear probabilities). Finally class C4, like C2, is relatively balanced along both axis.

Gender conditional classification probabilities are presented in Table 7. It is know from epidemiology litterature that women are more susceptible to OA. Hence it should be expected that female distribution among classes would be more focused on damaged classes. A possible sorting of classes in increasing pathological gravity order could be: C2, C3, C4 and C1. Note that females are mostly concentrated in class C1 (highest gravity) whereas male are concentrated in class C2 (lowest gravity).

TABLE 7

| | Classes: | | | | |
|---|---|---|---|---|---|
| | $C_1$ | $C_2$ | $C_3$ | $C_4$ | $C_5$ |
| P($C_i$/Male) | 0.2286 | 0.4286 | 0.2286 | 0.0571 | 0.0571 |
| P($C_i$/Female) | 0.4265 | 0.2647 | 0.1176 | 0.1618 | 0.0294 |

The present invention has now been described in connection with a number of specific embodiments thereof. However, numerous modifications which are contemplated as falling within the scope of the present invention should now be apparent to those skilled in the art. For example, the techniques described may be used in veterinary applications or for the imaging of other types of structures in the body. Another approach to normalization of joint structures is to employ landmark extraction and dense mesh correspondence. Therefore, it is intended that the scope of the present invention be limited only by the scope of the claims appended hereto. In addition, the order of presentation of the claims should not be construed to limit the scope of any particular term in the claims.

What is claimed is:

1. A musculoskeletal imaging system, comprising:
   a source of patient imaging data resulting from an imaging acquisition from a joint of a patient,
   a source of feature data extracted from imaging data resulting from imaging acquisitions from joints of different individuals affected by different diseases, wherein the feature data includes disease characteristic categorization information for a plurality of disease categories, and
   a comparison module that is operative to compare the patient imaging data with the feature data, and is operative to provide at least one categorization indicator for the patient imaging data that indicates a correspondence between spatial information in the patient imaging data and the disease categories for which there is extracted categorization information in the feature data.

2. The apparatus of claim 1 wherein the source of feature data is operative to provide feature data for at least some individuals having healthy cartilage.

3. The apparatus of claim 1 wherein the source of feature data is operative to provide feature data that expresses information for a plurality of patients that has been normalized and aggregated.

4. The apparatus of claim 3 wherein the source of feature data is operative to provide feature data that expresses information for a plurality of patients that has been normalized, aggregated, and compressed.

5. The apparatus of claim 3 wherein the source of feature data is operative to provide feature data that expresses information for a plurality of patients that has been normalized and averaged.

6. The apparatus of claim 3 wherein the source of feature data is operative to provide feature data that expresses information for a plurality of segmented patient scans that have been normalized and aggregated.

7. The apparatus of claim 6 wherein the source of feature data includes categorization information for a global significant cartilage loss category, for a global cartilage loss tendency category, for a medial condyle significant loss and medial trochlea loss tendency category, and for a medial condyle significant loss, trochlea significant loss, and medial condyle loss category.

8. The apparatus of claim 3 wherein the source of feature data is operative to provide feature data that expresses information for a plurality of segmented patient scans that have been normalized, aggregated, and compressed.

9. The apparatus of claim 1 wherein the comparison module is further operative to provide a confidence level for the categorization indicator.

10. The apparatus of claim 1 further including a follow-up module operative to identify trends in changes to the categorization indicator over time.

11. The apparatus of claim 1 further including an outgoing communication interface responsive to the comparison module and operative to provide the categorization indicator to a remote location.

12. The apparatus of claim 1 wherein the source of patient imaging data comprises part of an incoming communication interface.

13. The apparatus of claim 1 further including an aggregate result analysis module operative to perform statistical analysis of results from the comparison module for a plurality of patients.

14. The apparatus of claim 13 wherein the aggregate result analysis module includes correlative logic operative to determine relationships between treatment methods and categorization indicators for the plurality of patients.

15. The apparatus of claim 1 further including a classification adjustment module responsive to the comparison module and operative to adjust the categorization information based on results from the comparison module.

16. The apparatus of claim 1 wherein the disease characteristic categorization information includes a plurality of subcategories for different patient groupings.

17. The apparatus of claim 16 wherein the subcategories are based on symptom groupings.

18. The apparatus of claim 16 wherein the subcategories are based on patient demographic groupings.

19. The apparatus of claim 1 wherein the feature data further includes further patient characteristics extracted from additional sources.

20. The apparatus of claim 19 wherein the further patient characteristics include patient demographic information.

21. The apparatus of claim 19 wherein the further patient characteristics include patient symptom information.

22. The apparatus of claim 1 wherein the source of feature data is a source of imaging data resulting from statistical analysis of image data acquired from the joints affected by different diseases.

23. The apparatus of claim 22 wherein the source of feature data is a source of imaging data resulting from dispersion analysis of image data acquired from the joints affected by different diseases.

24. The apparatus of claim 1 wherein the source of feature data is a source of imaging data resulting from principal component analysis of image data acquired from the joints affected by different diseases.

25. The apparatus of claim 1 wherein the source of feature data includes categorization information for a global significant cartilage loss category and for at least one localized significant cartilage loss category.

26. The apparatus of claim 25 wherein the source of feature data includes categorization information for a global significant cartilage loss category, for a global cartilage loss tendency category, and for at least one localized significant cartilage loss category.

27. The apparatus of claim 1 wherein the source of patient imaging data is operative to provide a fully automatically segmented imaging data set.

28. The apparatus of claim 1 wherein the source of patient imaging data is operative to provide a imaging data set having a resolution that is significantly lower than a resolution for the acquisitions on which the feature data is based.

29. The apparatus of claim 1 wherein the source of patient imaging data includes digital identifiers associated with imaging data for a particular patient.

30. The apparatus of claim 29 wherein the digital identifiers include patient identifiers, physician identifiers, and joint identifiers.

31. The apparatus of claim 1 wherein the source of patient imaging data includes error correcting codes.

32. The apparatus of claim 31 wherein the error correcting codes include codes associated with imaging data for a particular patient.

33. The apparatus of claim 1 wherein the source of patient imaging data includes a format identifier associated with imaging data for a particular patient.

34. The apparatus of claim 1 further including a patient verification module.

35. The apparatus of claim 1 wherein the source of patient imaging data is a source of magnetic imaging data resulting from a magnetic resonance imaging acquisition from the joint of the patient.

36. A musculoskeletal imaging method, comprising:
obtaining a patient imaging data set resulting from an imaging acquisition from a joint of a patient,
obtaining feature data resulting from imaging acquisitions from joints of different individuals affected by different diseases, wherein the feature data includes extracted disease characteristic categorization information for a plurality of disease categories,
comparing the patient imaging data set with the feature data, and
providing, based on results of the step of comparing, a categorization indicator for the patient imaging data set that indicates a correspondence between information in the patient imaging data set and the extracted disease categories for which there is extracted categorization information in the feature data.

37. The method of claim 36 further including the step of determining whether to indicate a treatment for the patient based on the categorization indicator.

38. The method of claim 37 wherein the step of determining is operative to determine whether to indicate the use of a drug therapy.

39. The method of claim 38 wherein the step of determining is operative to determine whether to indicate the use of a disease modifying osteoarthritis drug.

40. The method of claim 38 wherein the step of determining is operative to determine whether to indicate the local administration of an anti-inflammatory agent.

41. The method of claim 37 wherein the step of determining is operative to determine whether to indicate the use of an exercise therapy.

42. The method of claim 37 wherein the step of determining is operative to determine whether to indicate surgery.

43. The method of claim 37 wherein the step of determining is operative to determine whether to indicate a rehabilitation method.

44. The method of claim 36 further including the step of determining whether to admit the patient to a clinical trail based on the categorization indicator.

45. The method of claim 36 further including the step of deriving from the categorization indicator and from other categorization indicators for other patients information about a treatment performed to at least some of the patients.

46. The method of claim 36 further including the step of determining whether to indicate a sports training regimen based on the categorization indicator.

47. The method of claim 36 further including the step of comparing the categorization indicator with results from other diagnostic methods.

48. The method of claim 36 wherein the step of obtaining a patient imaging data set includes obtaining a magnetic resonance imaging data set resulting from a magnetic resonance imaging acquisition from the joint of the patient.

49. A musculoskeletal imaging system, comprising:
- means for obtaining a patient imaging data set resulting from an imaging acquisition from a joint of a patient,
- means for obtaining feature data resulting from imaging acquisitions from joints of different individuals affected by different diseases, wherein the feature data includes extracted disease characteristic categorization information for a plurality of disease categories,
- means for comparing the patient imaging data set with the feature data, and
- means for providing, based on results of the step of comparing, a categorization indicator for the patient imaging data set that indicates a correspondence between information in the patient imaging data set and the extracted disease categories for which there is extracted categorization information in the feature data.

* * * * *